United States Patent [19]

Itoh et al.

[11] Patent Number: 5,280,114
[45] Date of Patent: Jan. 18, 1994

[54] HALOGENATION OF ALKOXYPHTHALOCYANINE

[75] Inventors: Hisato Itoh; Takahisa Oguchi; Shin Aihara, all of Yokohama, Japan

[73] Assignees: Mitsui Toatsu Chemicals, Incorporated, Tokyo; Yamamoto Chemicals, Incorporated, Yao, both of Japan

[21] Appl. No.: 729,338

[22] Filed: Jul. 12, 1991

Related U.S. Application Data

[63] Continuation-in-part of Ser. No. 680,921, Apr. 5, 1991.

[30] Foreign Application Priority Data

Apr. 7, 1990 [JP] Japan .................................. 2-91361

[51] Int. Cl.⁵ .............................................. C09B 47/10
[52] U.S. Cl. ..................................... 540/122; 540/128; 540/140
[58] Field of Search ................ 540/122, 128, 138, 140

[56] References Cited

PUBLICATIONS

JP-221971 (1986), Abstract "Phthalocyanine Compounds".
Publication Board Report No. 25,625 and 65,657 (cited on page 1 of specification).

*Primary Examiner*—Thurman K. Page
*Assistant Examiner*—Jyothsna Venkat
*Attorney, Agent, or Firm*—Oblon, Spivak, McClelland, Maier & Neustadt

[57] ABSTRACT

Halogenated alkoxyphthalocyanine having a controlled grade of halogenation can be prepared by reacting a single compound or a mixture of phthalocyanine represented by the formula (1):

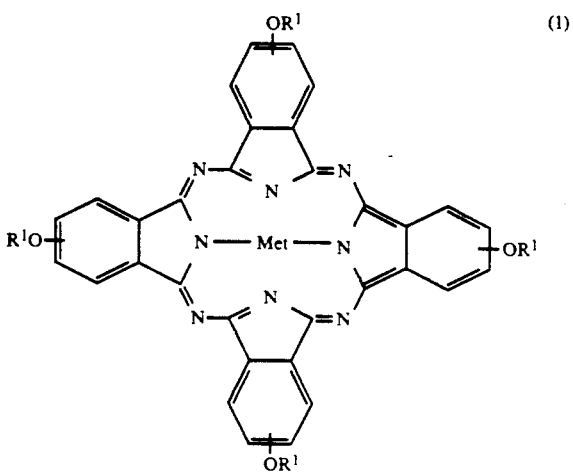

wherein $R^1$ is a substituted or unsubstituted alkyl group and may be the same or different, and Met is two hydrogen atoms, a divalent metal atom or a trivalent or tetravalent metal derivative, with 1 to 6 mole ratio of a halogenating agent at 0° to 260° C. in a solvent of from 1 to 1000 times by weight.

12 Claims, 3 Drawing Sheets

HALOGENATION OF ALKOXYPHTHALOCYANINE

This application is a continuation-in-part of parent application Ser. No. 07/680,921, filed Apr. 5, 1991, now pending.

BACKGROUND OF THE INVENTION

1. Field of the Invention

The present invention relates to a preparation process of phthalocyanine derivatives which are useful for dyes, pigments, photoelectric functional materials, recording and memory materials, and compact disk-write once type recording materials in particular. The invention also relates to a halogenated alcoxyphthalocyanine compound and a mixture of the same. Further, the invention relates to an optical recording medium comprising said phthalocyanine compound.

2. Description of the Related Art

Halogenation of phthalocyanine was described in Publication Board Report No. 25,625 and 65,657, and antimony trisulfide or aluminum chloride was used for the catalyst. Consequently, the process could not be applied to phthalocyanines having a readily releasable group such as an alkoxy group. Benzene substituted with an alkoxy group, i.e., ether is decomposed into phenol and alcohol in the presence of aluminum chloride or aluminum bromide. The reaction was reported in the literatures, Chem. Ber., 76B, 900 (1943), J. Org. Chem. 27, 2037 (1962), and Chem. Ber., 93, 2761 (1960). Acids generated as byproducts in halogenation, for example, hydrochloric acid and hydrobromic acid in halogenation by chlorine and bromine, are known as reagents for decomposing the above ether to phenol and alcohol [J. Org. Chem., 6, 852 (1941), Chemical Industries, 1967, 1138].

Preparation process of halogenated alkoxyphthalocyanine has been disclosed in Japanese Laid-Open Patent 85630 (1975) and J. Chem. Soc., Perkin Trans. I, 1988, 2453–2458. In the former process, halogenated phthalocyanine is substituted with alkali metal aliphatic alcoholate or alkali metal phenolate to obtain the desired halogenated alkoxyphthalocyanine or halogenated aryloxyphthalocyanine. In the latter process, the desired halogenated alkoxyphthalocyanine is prepared by by ring closure of dialkoxy-dihalogenophthalonitrile. However, these processes could not be applied to introduce 1 to 4 halogen atoms into tetraalkoxyphthalocyanine.

The inventors have investigated on a recording material suitable for a compact disk-write once type recording medium (hereinafter referred to as CD-WO) and obtained following information.

(1) CD-WO utilizes laser beams in the neighborhood of 780 nm for write and read of record and it is hence important to control absorption coefficient, refractive index and reflectance of the recording material in the neighborhood of 780 nm.

(2) Halogenated alkoxyphthalocyanine is suitable for enhancing sensitivity of CD-WD because decomposition process of phthalocyanine can be controlled by mutual action of the alkoxy groups and the halogen atoms.

The substitution positions of the alkoxy groups are preferably the positions illustrated in the below formulas (9) to (12). A mixture composed of 5 or more isomers or a mixture of compounds having different grade of halogenation is particularly preferred in these halogenated alkoxyphthalocyanines.

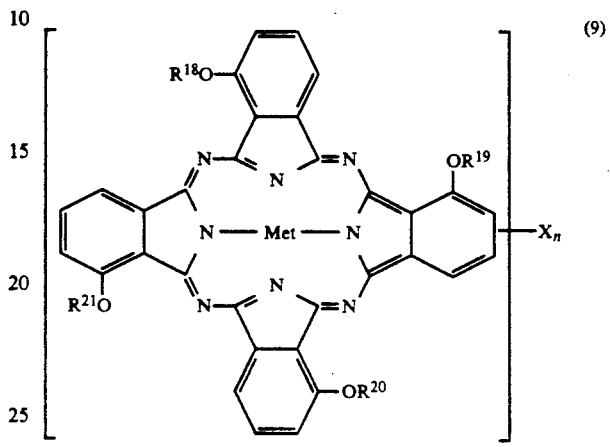

(9)

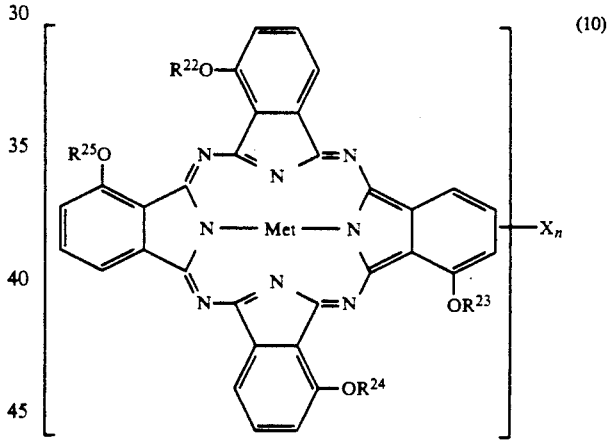

(10)

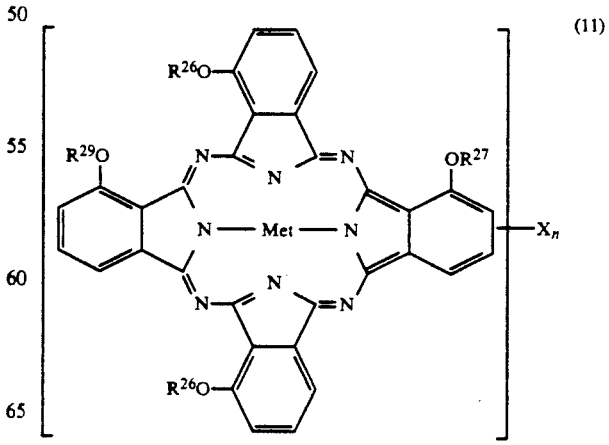

(11)

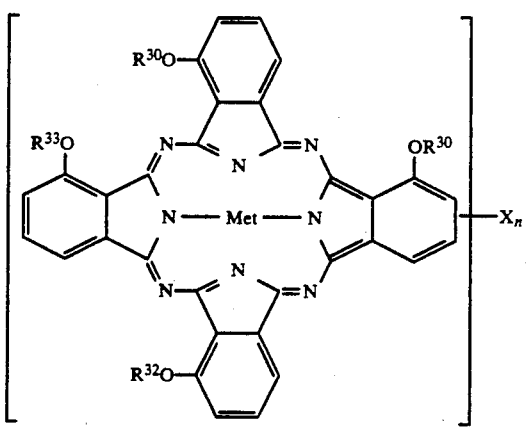

wherein each $R^{18}$ to $R^{33}$ is individually a substituted or unsubstituted alkyl group, X is a halogen atom, n indicates numbers of X and is an integer of from 1 to 4, and Met is two hydrogen atoms, a divalent metal atom, or a derivative of trivalent or tetravalent metal. Particularly preferred phthalocyanine is a compound wherein alkoxy groups are secondary, the sum of secondary to quaternary carbon atoms is from 2 to 4, and halogen is bromine.

(3) CD-WO is required to have reflectance of 65% or more. Accordingly, the recording material must have a high refractive index. The inventors have found that refractive index can be improved by introducing an alkoxy group having large steric hindrance into phthalocyanine and further enhanced by additionally introducing a halogen atom, a bromine atom in particular, into the resultant alkoxyphthalocyanine.

(4) In the application of the recording material to a substrate of the recording medium by a solvent casting method such as a spin coating method which is favorable in industry, solubility of the recording material in solvent is an important factor for forming an uniform recording layer.

SUMMARY OF THE INVENTION

The object of the present invention is to provide a preparation process of the above halogenated alkoxyphthalocyanine having a controlled grade of halogenation.

Another object of the invention is to provide a halogenated alkoxyphthalocyanine having excellent properties as a recording material for CD-WO.

A further object of the present invention is to provide an optical recording medium comprising the above halogenated alkoxyphthalocyanine in the recording layer.

As a result of an intensive investigation in order to accomplish these objects, the present inventors have found that halogenated alkoxyphthalocyanine having a controlled grade of halogenation can be obtained by reacting alkoxyphthalocyanine in a halogenated hydrocarbon or aliphatic carboxylic acid solvent under specific reaction temperature and amount of the solvent. Thus the present invention has been completed.

According to the prior art, hydroxyphthalocyanine which is a decomposition product of ether naturally generates in a large amount as a byproduct of the reaction. However, in the practice of the invention, the amount of the byproduct hydroxyphthalocyanine is surprisingly very small and gives almost no adverse effect on the quality of the desired product.

That is, the object of the present invention has been achieved by halogenating a single compound or a mixture of phthalocyanine represented by the formula (1):

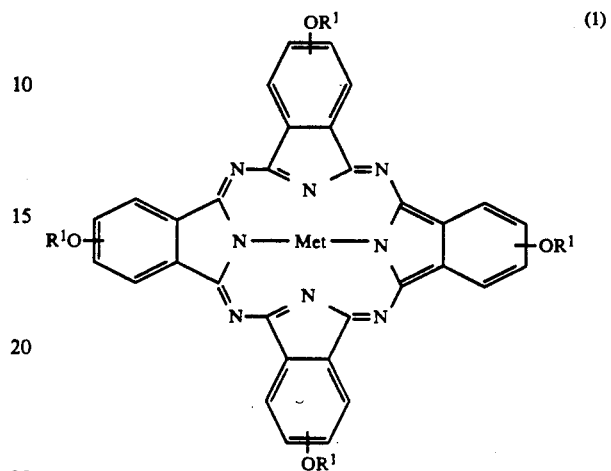

wherein $R^1$ is a substituted or unsubstituted alkyl group and may be the same or different, and Met is two hydrogen atoms, a divalent metal atom, or a trivalent or tetravalent metal derivative, in 1 to 1000 times by weight of a solvent at a temperature of 0° to 250° C. with 1 to 6 molar ratio of a halogenating agent. In order to obtain an optimum amount of the halogen atom introduced in particular, the reaction is preferably carried out by using the solvent at 5 to 100 times the amount of alkoxyphthalocyanine at a reaction temperature of 20° to 120° C. with a halogenating agent mole ratio of 1 to 6. The kind or amount of the solvent is optimized depending upon the solubility of alkoxyphthalocyanine having the formula (1) in the solvent.

DETAILED DESCRIPTION OF THE PREFERRED EMBODIMENTS

Figure 1:
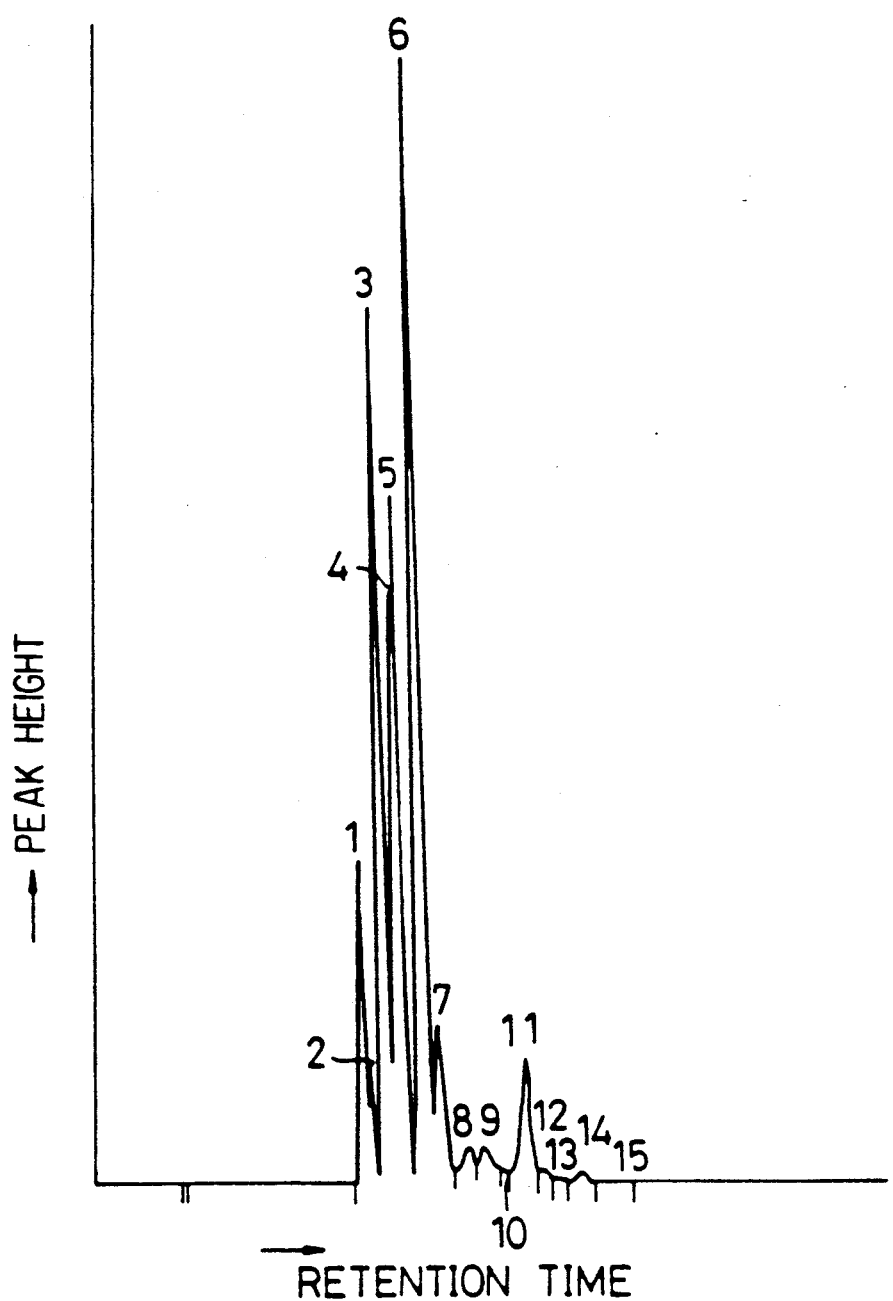
FIGS. 1, 2 and 3 are charts of high performance liquid chromatography on the mixtures obtained in Examples 12, 13 and 14, respectively.

Particularly preferred alkoxyphthalocyanine as a raw material of the invention is α-alkoxyphthalocyanine represented by the formula (4) to formula (7):

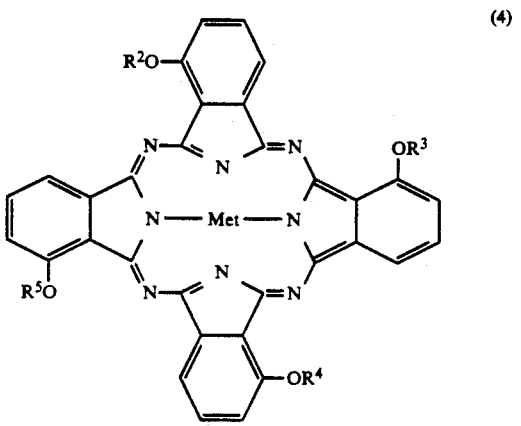

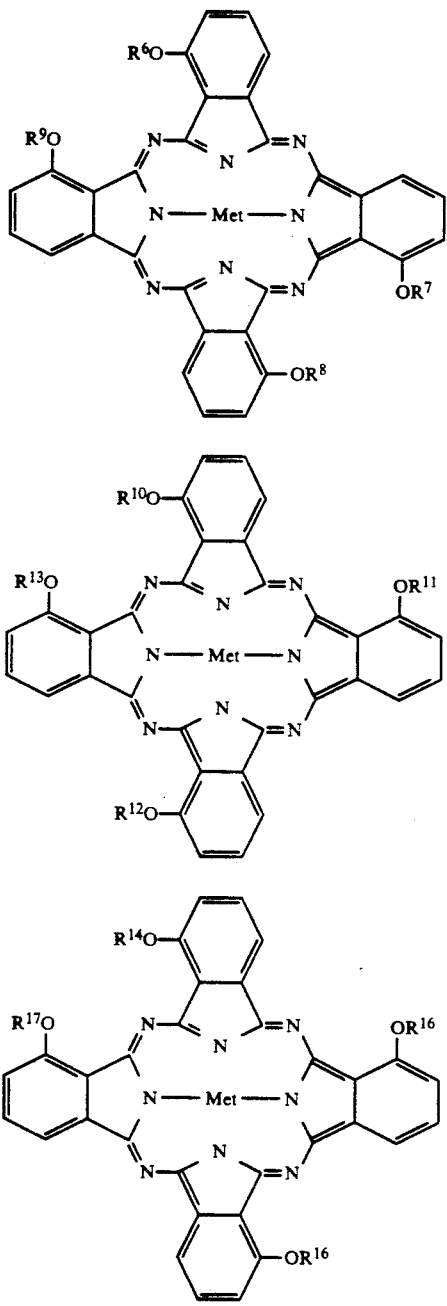

wherein each of $R^2$ to $R^{17}$ is individually a substituted or unsubstituted alkyl group, Met is two hydrogen atoms, a divalent metal atom, or a trivalent or tetravalent metal derivative. A mixture of these α-alkoxyphthalocyanines is preferably used depending upon the desire.

In the above alkoxyphthalocyanines, $R^2$ to $R^{17}$ are preferably secondary alkyl groups, more preferably alkyl groups having the sum of 2 to 4 of secondary, tertiary and quaternary carbon atoms.

Exemplary alkyl groups which are represented by $R^1$ to $R^{17}$ in the formulas (1) and (4) to (7) include hydrocarbon groups such as a methyl, ethyl, n-propyl, isopropyl, n-butyl, isobutyl, sec-butyl, t-butyl, n-pentyl, iso-pentyl, neo-pentyl, 1,2-dimethylpropyl, n-hexyl, cyclohexyl, 1,3-dimethylbutyl, 1-iso-propylpropyl, 1,2-dimethylbutyl, n-heptyl, 1,4-dimethylpentyl, 2-methyl-1-iso- propylpropyl, 1-ethyl-3-methylbutyl, n-octyl, 2-ethylhexyl, 3-methyl-1-isopropylbutyl, 2-methyl-1-isopropylbutyl, 1-t-butyl-2-methylpropyl, and n-nonyl group; alkoxyalkyl groups such as a methoxymethyl, methoxyethyl, ethoxyethyl, propoxyethyl, butoxyethyl, methoxyethoxyethyl, ethoxyethoxyethyl, dimethoxymethyl, diethoxymethyl, dimethoxyethyl, and diethoxyethyl group; and halogenated alkyl groups such as a chloromethyl, 2,2,2-trichloromethyl, trifluoromethyl, and 1,1,1,3,3,3-hexafluoro-2-propyl group.

Preferred alkyl groups contain 2 to 4 carbon atoms consisting of the sum of secondary, tertiary and quaternary carbon atoms and are 1,2-dimethylpropyl, 1,3-dimethylbutyl, 1-isopropylpropyl, 1,2-dimethylbutyl, 1,4-dimethylpentyl, 2-methyl-1-isopropylpropyl, 1-ethyl-3-methylbutyl, 3-methyl-1-isopropylbutyl, 2-methyl-1-isopropylbutyl and 1-t-butyl-2-methylpropyl group.

In the formulas (1) and from (4) to (7), exemplary divalent metals represented by Met include Cu, Zn, Fe, Co, Ni, Ru, Rh, Pd, Pt, Mn and Sn; exemplary monosubstituted trivalent metals of Met include Al-Cl, Al-Br, In-Cl, In-Br and In-I; exemplary disubstituted tetravalent metals of Met include $SiCl_2$, $SiBr_2$, $SiF_2$, $SnCl_2$, $SnBr_2$, $SnF_2$, $GeCl_2$, $GeBr_2$, $GeF_2$, $Si(OH)_2$, $Sn(OH)_2$ and $Ge(OH)_2$; and exemplary oxy metals include VO and TiO. Particularly preferred metals are Cu, Ni, Pd and Pt.

The halogenating agent which can be used in the invention is a compound represented by the formula (II):

$$X—Y \qquad (2)$$

wherein X is a halogen atom and Y is a residue of the halogenating agent. The halogen atom includes F, Cl, Br and I. Br is preferred. The residue of the halogenating agent includes Cl, Br, I, $SO_2Cl$, SOCl, $FeCl_2$ $PCl_4$, $POCl_2$, CuBr and quaternary ammonium.

Exemplary halogenating agents include chlorine, bromine, iodine, sulfuryl chloride, thionyl chloride, antimony chloride, $ICl_3$, $FeCl_3$, phosphorus pentachloride, phosphorus oxychloride, t-butyl hypochlorite, N-chlorosuccinic imide, cupric bromide, quaternary ammonium bromide, N-bromosuccinic imide, iodine monochloride, quaternary ammonium iodide, and potassium triiodide. Bromine is preferred in particular.

The halogenating agent is suitably used in the range of 1 to 6 mole ratio depending upon the desired amount of the halogen to be introduced. Distinct characteristics are found when bromine is used in particular. In the case of using 2 moles of bromine per mole of alkoxyphthalocyanine, 1, 2, 3 or 4 atoms of bromine is introduced. In the case of using 2.5 to 4.0 moles of bromine, 2, 3 or 4 atoms of bromine is introduced. Maximum number of introduced bromine atoms is 4, though more than 4 moles of bromine is used.

Halogenated hydrocarbons which are used for the solvent include, for example, carbon tetrachloride, chloroform, dichloromethane, 1,1,1-trichloroethane, 1,1,2-trichloroethane, tetrachloroethylene and 1,1,2,2-tetrachloroethane. Aliphatic carboxylic acids used for the solvent include, for example, acetic acid.

The alkoxyphthalocyanines represented by the formulas (1) and from (4) to (7) were prepared by the process described in U.S. Pat. No. 4,769,307 and Nouveau Journal de Chimie, Vol. 6, No. 12, 653–658 (1982).

The reaction was carried out according to the reaction formula (13):

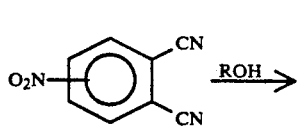
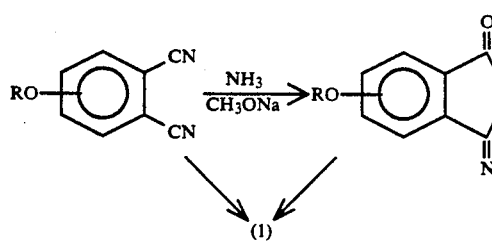

(13)

Alcohol was reacted with sodium hydride at 0° to 30° C. to obtain sodium alkoxide, succssively nitrophthalonitrile was added and reacted at 0° to 100° C. to obtain alkoxyphthalonitrile. The resulting alkoxyphthalonitrile was reacted with 0.8 to 1.2 mole ratio of a metal salt in alcohol at 100° to 300° C. to obtain alkoxyphthalocyanine. Alkoxyphthalocyanine can also be obtained similarly by converting alkoxyphthalonitrile to diiminoisoindoline and successively reacting with the metal salt.

The halogenated alkoxyphthalocyanine prepared under the above reaction conditions is represented by the formula (3):

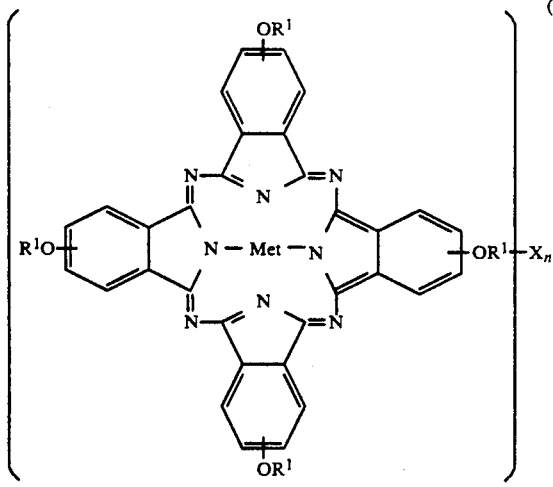

(3)

wherein $R^1$, Met and X are the same as $R^1$ and Met in the formula (1) and X in the formula (2), and n is a substitution number of X and is an integer of 1 to 4.

The halogenated alkoxyphthalocyanine is preferably a compound of a mixture of the compound represented by the formula (9) to formula (12):

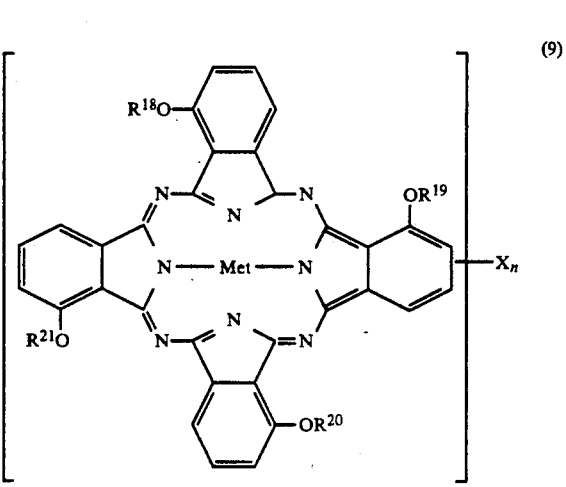

(9)

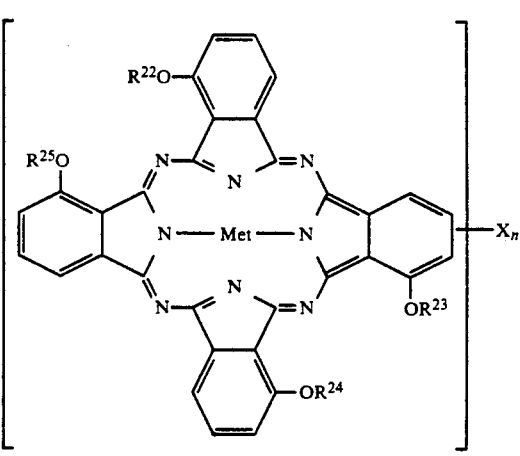

(10)

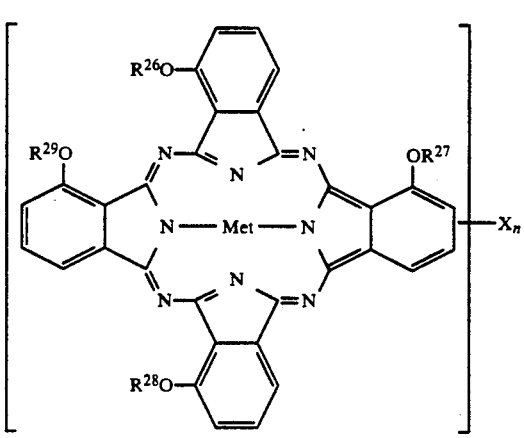

(11)

-continued

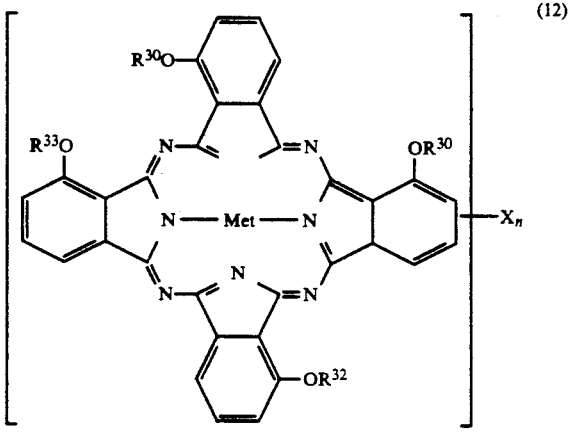

(12)

wherein each of $R^{18}$ to $R^{33}$ is individually a substituted or unsubstituted alkyl group, X is a halogen atom, n is a number of X and is an integer of from 1 to 4, and Met is two hydrogen atoms, a divalent metal atom, or a trivalent or tetravalent metal drivative.

Particularly preferred, halogenated alkoxyphthalocyanine is a compound wherein $R^{18}$ to $R^{33}$ are secondary alkyl groups and particularly have 2 to 4 carbon atoms in the sum of secondary, tertiary and quaternary carbon atoms, and the halogen is bromine.

The halogenated alkoxyphthalocyanine thus prepared is a mixture of five or more isomers or compounds having a different bromine content. The optical recording medium prepared by using the mixture without separating each component can satisfy the above objects. The mixture does not deteriorate performance for the optical recording medium, though ratio of the component is varied. However, a single compound or a mixture of two or three kinds of the compound cannot fully satisfy the above objects.

An optical recording medium which comprises the halogenated alkoxyphthalocyanine described above, has good quality.

The medium can be manufactured by the following process:

The medium is substantially composed of a transparent substrate and recording layer. If desired, the medium has also an optical reflective layer and a protective layer.

The substrate can be made from an optically transparent resin. Examples of such resin include acrylic resin, polyethylene resin and polycarbonate resin. Furthermore, the substrate may be surface-treated with a thermosetting resin or an ultraviolet-setting resin.

The recording layer can be prepared by coating the above compounds on the substrate. In the coating method, a binder resin and the above compounds are dissolved in a solvent so that concentration of the binder resin and the above compounds may be 20% by weight or less, preferably 0%, i.e., absent and 0.05 to 20% by weight, preferably 0.5 to 20% by weight, respectively, and then application is carried out by using a spincoater. The thickness of the recording layer is preferably from 50 to 300 nm.

Considering solvent resistance of the substrates, such a solvent as exemplified below is preferably used in the spin coating. Examples of such preferably usable solvents include halogenated hydrocarbons such as dichloromethane, chloroform, carbon tetrachloride, trichloroethane, dichloroethane, tetrachloroethylene and dichlorodifluoroethane; ethers such as diethyl ether, dipropyl ether, dibutyl ether and dioxane; alcohols such as methanol, ethanol, propanol and butanol; cellosolves such as methyl cellosolve, ethyl cellosolve, propyl cellosolve and butylcellosolve; ketones such as trifluoroacetone, hexafluoroacetone and hexafluoro-2-butanone; and hydrocarbons such as hexane, octane, cyclo-hexane and cyclo-octane.

The reflective layer comprises aluminum or gold. The reflective layer can be prepared by vapor depositing or sputtering. The thickness of the reflective layer is preferably 1 to 200 nm.

Preferred protective layer is transparent and can be prepared by applying an ultraviolet curing resin or thermosetting resin with a spin coater and then curing the resin. The thickness of the protective layer is preferably from 1 to 500 μm.

When the optical recording media are manufactured, it is preferred from the viewpoints of cost and users' handling that the polyacrylate or polycarbonate substrate is employed and that the application is made by the spin coating technique.

The present invention will hereinafter be illustrated in detail by way of examples. However, these examples are not construed to be limiting the scope of the invention. Part or parts used in the examples mean part or parts by weight.

EXAMPLE 1

Ten parts of palladium tetra(1,3-dimethylpropyloxy)phthalocyanine was dissolved in 1000 parts of carbon tetrachloride. Two parts of bromine were added dropwise to the solution at 40° C. and reacted for 3 hours. Precipitated crystals were filtered, washed and dried to obtain 5 parts of a colorant mixture of the formulas (14) and (15):

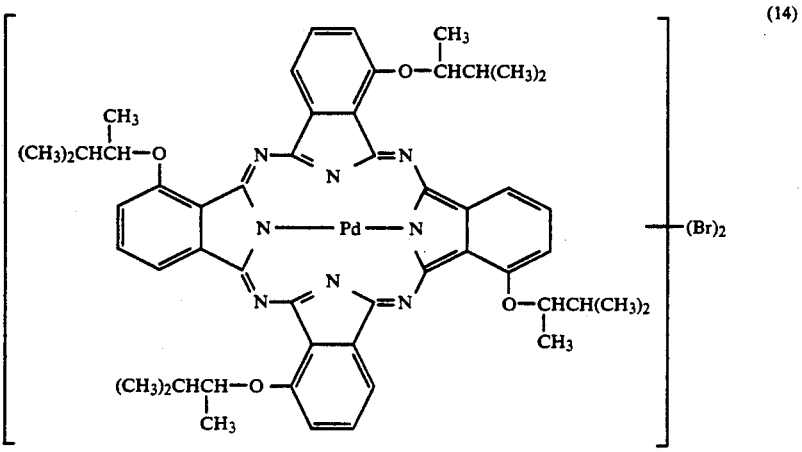

(14)

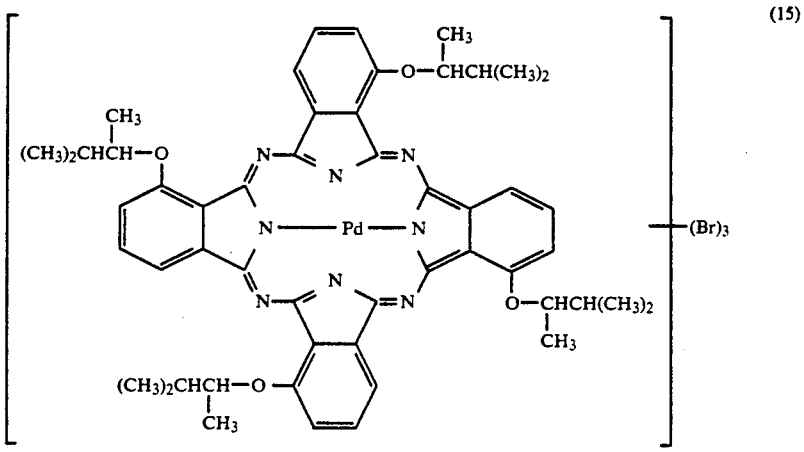

(15)

The colorant mixture had a melting point of 170° to 200° C. and a decomposition initiating temperature of 305° C.

A solution obtained by dissolving 5 parts of the mixture in 500 parts of n-octane was coated with a spin coater on a polycarbonate substrate for CD-WO to obtain a dried film thickness of 150 nm. Gold was sputtered on the coated surface to obtain a film thickness of 30 nm and successively an ultraviolet curing resin was coated on the gold layer to form a protective layer by curing the resin.

The CD-WO type medium thus obtained had a reflection of 65%, and could be written a record having a C/N ratio of 65 dB at a linear velocity of 1.4 m/sec with a laser beam of 7 mW in power and 790 nm in wavelength. The recording medium had no change after a light resistance test with a carbon-arc lamp at 63° C. for 200 hours.

EXAMPLE 2

Ten parts of palladium 1,5,9,13-tetra(2,4,4-trimethyl-3-hexyloxy)phthalocyanine were dissolved in 1000 parts of acetic acid, and 10 parts of iodine were added and reacted at 50° C. for 3 hours. Precipitated crystals were filtered and purified to obtain a colorant mixture illustrated by the formula (16):

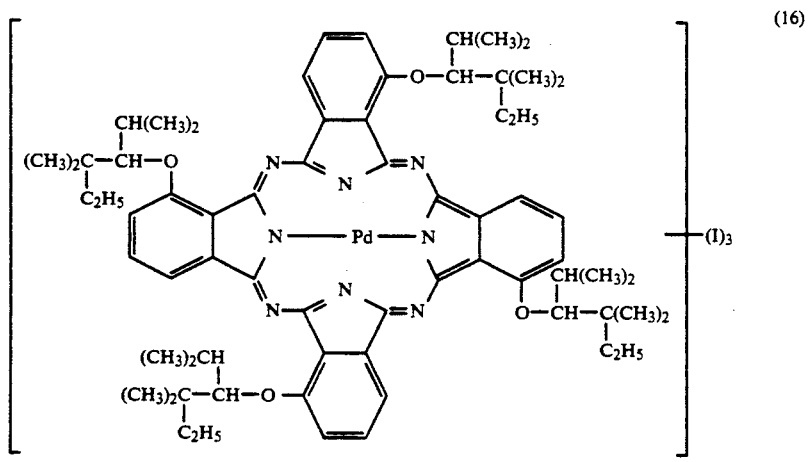

(16)

The mixture had a melting point of 200° to 245° C., decomposition initiating temperature of 285° C., λmax of 708 nm and εmax of $1.5 \times 10^5$ 1 $mol^{-1}$ $cm^{-1}$.

A solution obtained by dissolving 5 parts of the colorant mixture in n-octane was coated on a polycarbonate substrate for CD-WO with a spin coater to obtain a film thickness of 120 nm. Gold was vapor deposited on the coated layer to a thickness of 50 nm and successively a protective layer was formed by using an ultraviolet curing resin.

The CD-WO medium thus obtained was written a record at a linear velocity of 1.3 m/sec with a laser of 7 mW in power and 780 nm in wavelength to obtain the record having a C/N ratio of 55 dB. The recording medium had no change after a light resistance test with a xenon lamp at 50° C. for 200 hours.

EXAMPLE 3

Fifteen grams of palladium tetra-α-(1,3-dimethylbutyloxy)phthalocyanine were added to 375 ml of carbon tetrachloride and dissolved by warming to 45° C. Thereafter 19 g of bromine was added dropwise to the solution and stirred at 50° C. for an hour. The reaction mixture was cooled to 40° C. Precipitated crystals were filtered and sludged three times with 200 ml of methanol. The crystals obtained were dried under reduced pressure. The yield was 17.7 g.

Elementary analysis proved that the number of bromine substitution was 3.

| Elementary analysis: $C_{56}H_{61}N_8O_4Br_3Pd$ | | | | |
|---|---|---|---|---|
| | C | H | N | Br |
| Calculated (%) | 53.54 | 4.89 | 8.92 | 19.08 |
| Found (%) | 52.86 | 4.67 | 8.68 | 19.41 |

EXAMPLE 4

Ten grams of palladium tetra-α-(1,3-dimethylbutyloxy)phthalocyanine were added to 150 ml of carbon tetrachloride and dissolved by warming to 40° C. Thereafter 6 g of bromine was added dropwise to the solution and stirred at 40° C. for 30 minutes. The reaction mixture was allowed to stand at the same temperature. Precipitated crystals were filtered and sludged three times with 100 ml of methanoal. The crystals obtained were dried under reduced pressure. The yield was 11 g.

Elementary analysis proved that the number of bromine substitution was 2.

| Elementary analysis: $C_{56}H_{62}N_8O_4Br_2Pd$ | | | | |
|---|---|---|---|---|
| | C | H | N | Br |
| Calculated (%) | 57.13 | 5.31 | 9.52 | 13.57 |
| Found (%) | 56.76 | 5.59 | 9.28 | 13.83 |

EXAMPLE 5

Ten grams of palladium tetra-α-(1-isopropyl-2-methylbutyloxy)phthalocyanine were added to 400 ml of 1,1,2-trichloroethane and dissolved by warming to 40° C. Thereafter 16 g of bromine was added dropwise to the solution and stirred at 70° C. for 5 hours. The reaction mixture was cooled to 40° C. Precipitated crystals were filtered and sludged three times with 100 ml of methanol. The crystals obtained were dried under reduced pressure. The yield was 12.3 g.

Elementary analysis proved that the number of bromine substitution was 4.

| Elementary analysis: $C_{60}H_{68}N_8O_4Br_4Pd$ | | | | |
|---|---|---|---|---|
| | C | H | N | Br |
| Calculated (%) | 51.80 | 4.93 | 8.05 | 23.97 |
| Found (%) | 51.56 | 5.20 | 8.21 | 23.33 |

EXAMPLE 6

Two grams of palladium tetra-α-(2-ethylhexyloxy)phthalocyanine were added to 400 ml of 1,1,2,2-tetrachloroethane and dissolved by warming to 40° C. Thereafter 5 g of bromine was added dropwise to the solution and stirred at 50° C. for an hour. The reaction mixture was cooled to 40° C. Precipitated crystals were filtered and sludged three times with 30 ml of methanol. The crystals obtained were dried under reduced pressure. The yield was 2.2 g. According to elementary analysis, the number of bromine substitution was between 2 and 3, and proved of a mixture consisting of 2 and 3 bromine-substituted phthalocyanine.

| Elementary analysis | | | | |
|---|---|---|---|---|
| | C | H | N | Br |
| Calculated (%) | | | | |

| Elementary analysis | | | | |
|---|---|---|---|---|
| | C | H | N | Br |
| 2-substitution | 59.60 | 6.10 | 8.69 | 12.39 |
| 3-substitution | 56.17 | 5.67 | 8.19 | 17.52 |
| Found (%) | 57.91 | 5.86 | 8.47 | 14.94 |

EXAMPLE 7

Five grams of dichlorosilicone tetra-α-(2-ethylhexyloxy)phthalocyanine were added to 100 ml of 1,1,1-trichloroethane and dissolved by warming to 40° C. Thereafter 5 g of bromine was added dropwise to the solution and stirred at 50° C. for an hour. The reaction mixture was cooled to 40° C. Precipitated crystals were filtered and sludged three times with 100 ml of methanol. The crystals obtained were dried under reduced pressure. The yield was 5.2 g. According to elementary analysis, the number of bromine substitution was 3.

| Elementary analysis: $C_{64}H_{77}N_8O_4Br_3Cl_2Si$ | | | | | |
|---|---|---|---|---|---|
| | C | H | N | Br | Cl |
| Calculated (%) | 56.48 | 5.70 | 8.23 | 17.61 | 5.21 |
| Found (%) | 57.05 | 5.85 | 8.33 | 17.01 | 5.38 |

EXAMPLE 8

Two grams of palladium tetra-α-(1,3-dimethylbutyloxy)phthalocyanine were added to 40 ml of carbon tetrachloride and dissolved by warming to 35° C. Thereafter 2 g of sulfuryl chloride was added dropwise to the solution and stirred at 50° C. for 1.5 hours. The reaction mixture was cooled to 35° C. Precipitated crystals were filtered, washed twice with 50 ml of water and sludged three times with 50 ml of methanol. The crystals obtained were dried under reduced pressure. The yield was 2.2 g. According to elementary analysis, the number of chlorine substitution was 4.

| Elementary analysis: $C_{56}H_{60}N_8O_4Cl_4Pd$ | | | | |
|---|---|---|---|---|
| | C | H | N | Cl |
| Calculated (%) | 58.11 | 5.23 | 9.68 | 12.25 |
| Found (%) | 57.73 | 5.10 | 9.58 | 12.65 |

EXAMPLE 9

Fifteen grams of palladium tetra-α-(1,3-dimethylbutyloxy)phthalocyanine were added to 375 ml of acetic acid and dissolved by warming to 45° C. Thereafter 19 g of bromine was added dropwise to the solution and stirred at 50° C. for an hour. The reaction mixture was cooled to 40° C. Precipitated crystals were filtered and sludged three times with 200 ml of methanol. The crystals thus obtained were dried under reduced pressure. The yield was 17.7 g. According to elementary analysis, the number of bromine substitution was 3.

| Elementary analysis: $C_{56}H_{61}N_8O_4Br_3Pd$ | | | | |
|---|---|---|---|---|
| | C | H | N | Br |
| Calculated (%) | 53.54 | 4.89 | 8.92 | 19.08 |
| Found (%) | 52.97 | 4.77 | 8.71 | 19.32 |

EXAMPLE 10

Ten grams of palladium tetra-α-(1,3-dimethylbutyloxy)phthalocyanine were added to 150 ml of acetic acid and dissolved by warming to 40° C. Thereafter 6 g of bromine was added dropwise to the solution and stirred at 40° C. for 30 minutes. The reaction mixture was maintained at the same temperature. Precipitated crystals were filtered and sludged three times with ml of methanol. The crystals thus obtained were dried under reduced pressure The yield was 11 g. According to elementary analysis, the number of bromine substitution was 2.

| Elementary analysis: $C_{56}H_{62}N_8O_4Br_2Pd$ | | | | |
|---|---|---|---|---|
| | C | H | N | Br |
| Calculated (%) | 57.13 | 5.31 | 9.52 | 13.57 |
| Found (%) | 56.67 | 5.50 | 9.39 | 13.80 |

EXAMPLE 11

Ten grams of palladium tetra-α-(1-isopropyl-2-methylbutyloxy)phthalocyanine were added to 400 ml of acetic acid and dissolved by warming to 40° C. Thereafter 16 g of bromine was added dropwise to the solution and stirred at 70° C. for 5 hours. The reaction mixture was cooled to 40° C. Precipitated crystals were filtered and sludged three times with 100 ml of methanol. The crystals thus obtained were dried under reduced pressure. The yield was 12.3 g. According to elementary analysis, the number of bromine substitution was 4.

| Elementary analysis: $C_{60}H_{68}N_8O_4Br_4Pd$ | | | | |
|---|---|---|---|---|
| | C | H | N | Br |
| Calculated (%) | 51.80 | 4.93 | 8.05 | 23.97 |
| Found (%) | 51.69 | 5.18 | 8.19 | 23.22 |

EXAMPLE 12

Ten grams of a mixture composed of the compounds having the formulas (17) and (18) in a (17)/(18) ratio of 95/5 were dissolved in 200 g of carbon tetrachloride.

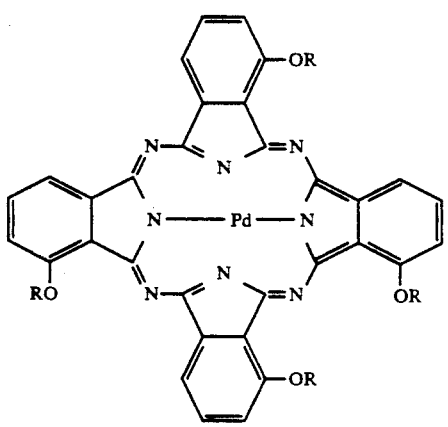

(17)

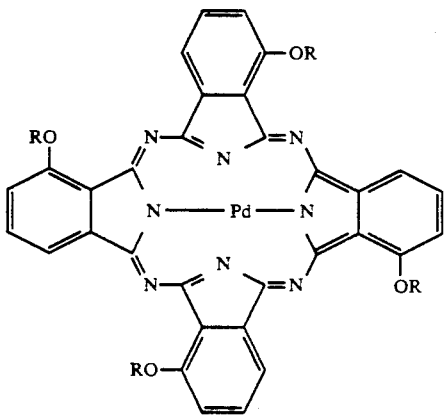

(18)

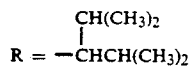

R = —CH(CH(CH₃)₂)CH(CH₃)₂

(where R = -CHCH(CH$_3$)$_2$ with CH(CH$_3$)$_2$ branch)

A solution containing 4.44 g of bromine in 10 g of carbon tetrachloride was added dropwise at 50° C. to the resulting solution and reacted for 30 minutes at 50°-60° C. The reaction mixture was cooled to room temperature and 50 g of a 10% aqueous sodium hydrogen-sulfite solution was added. The mixture was stirred at 60° C. for 30 minutes. Water layer was separated and the carbon tetrachloride layer was neutralized with a 5% aqueous sodium hydrogen carbonate solution. Water layer was separated again and the carbon tetrachloride layer was dried. Successively the carbon tetrachloride layer was poured into 1000 g of methanol and 6 g of a mixture represented by the formulas (19) and (20) was obtained:

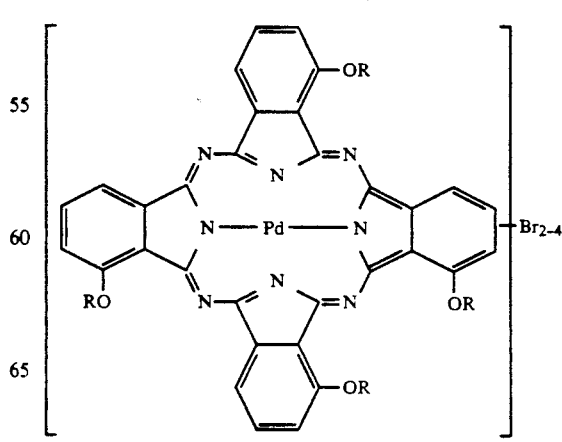

(19)

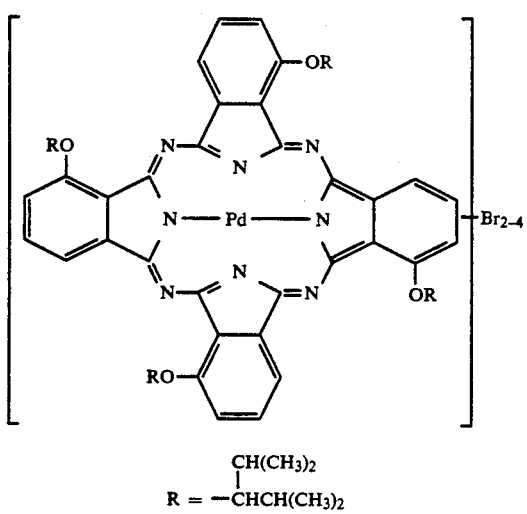

(20)

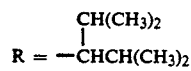

R = —CHCH(CH₃)₂ with CH(CH₃)₂ branch

The mixture has a maximum absorption wavelength of 705 nm. Mass spectrometry proved that the number of bromine substitution was a mixture of 2, 3 and 4. According to elementary analysis, the average bromination rate is 2.8 Br/molecule. Results of liquid chromatography and mass spectrometory proved that the number of bromine substitution was 2, 3 and 4. FIG. 1 illustrates the chart of liquid chromatography. Table 1 shows the concentration ratio of each peak in FIG. 1.

TABLE 1

| PKNO | RETENTION TIME | CONC. RATIO |
|---|---|---|
| 1 | 15.142 | 6.3916 |
| 2 | 15.588 | 2.1747 |
| 3 | 16.407 | 19.047 |
| 4 | 17.142 | 10.5829 |
| 5 | 17.438 | 15.043 |
| 6 | 18.642 | 30.7354 |
| 7 | 19.518 | 5.5061 |
| 8 | 21.09 | 1.6785 |
| 9 | 21.953 | 2.1142 |
| 10 | 23.125 | 0.3995 |
| 11 | 24.385 | 5.0455 |
| 12 | 25.192 | 0.4202 |
| 13 | 26.225 | 0.2142 |
| 14 | 27.287 | 0.5365 |
| 15 | 29.657 | 0.1108 |
| | TOTAL | 100 |

EXAMPLE 13

Ten grams of a mixture composed of the compounds having the above formulas (17) and (18) in a (17)/(18) ratio of 80/20 were added to 300 g of acetic acid. A solution containing 6.0 g of bromine in 20 g of carbon tetrachloride was added dropwise at 60° C. to the resulting solution and reacted for one hour at 60°–70° C. The reaction mixture was cooled to room temperature and 500 ml of toluene was added. The mixture was adjusted to pH 6 by the addition of a 5% aqueous sodium hydroxide solution. Thereafter 50 g of a 10% sodium hydrogen sulfite solution was added to carry out bromine-removing treatment at 50° C. for one hour. Water layer was removed and then toluene layer was dried. Toluene was distilled off and precipitated tar was sludged with methanol. Separated green crystals were filtered. The yield was 8 g.

The product thus obtained was a mixture of the compounds having the below described formulas (21), (22), (23), (24), (25) and (26):

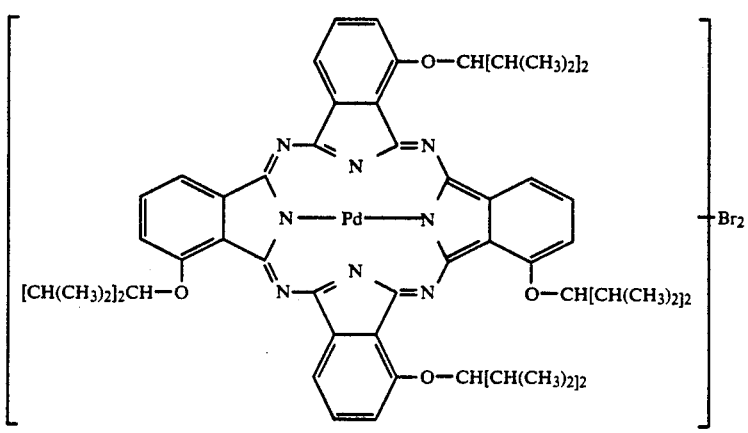

(21)

-continued
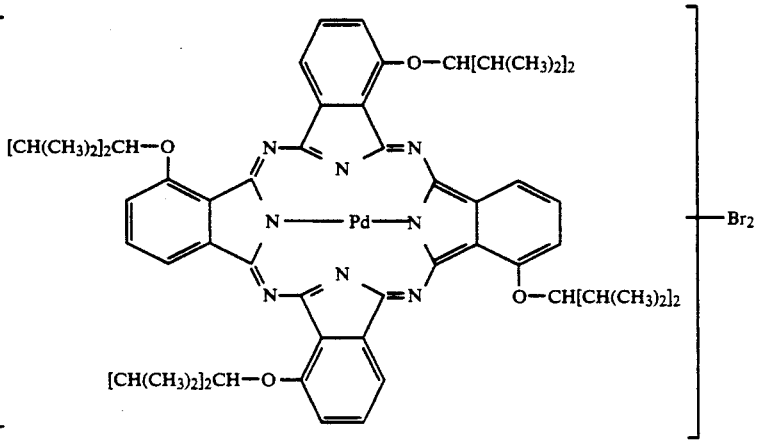
(22)
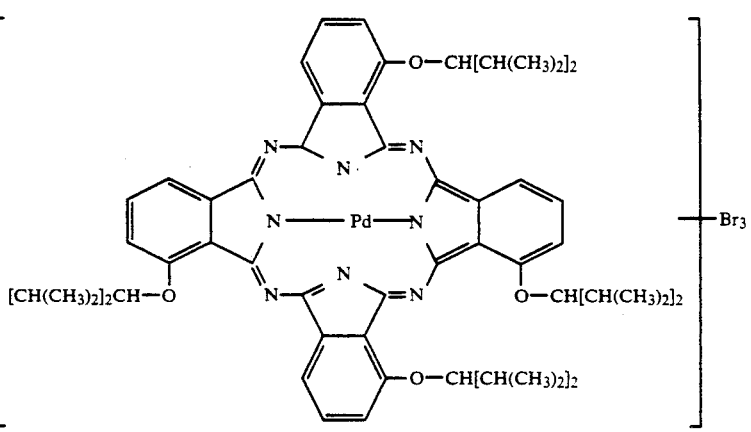
(23)
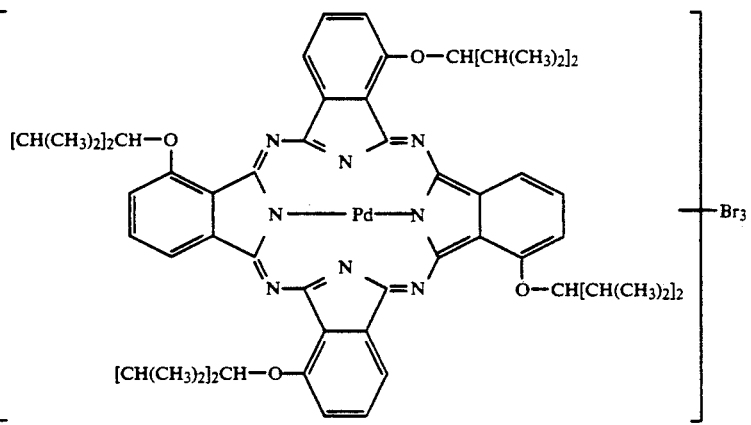
(24)

-continued

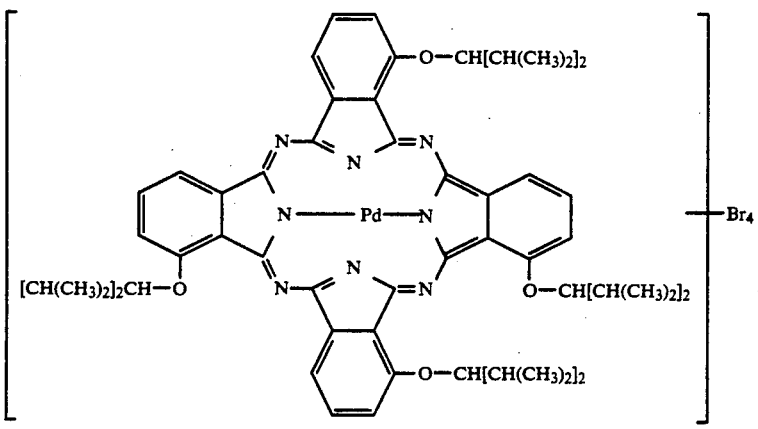

(25)

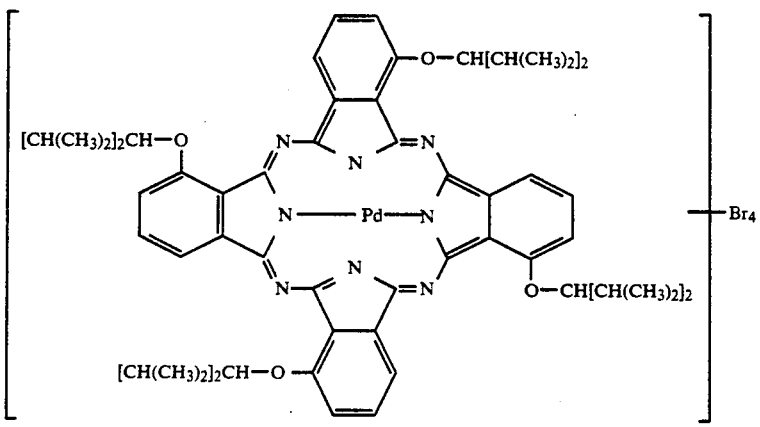

(26)

Figure 2:
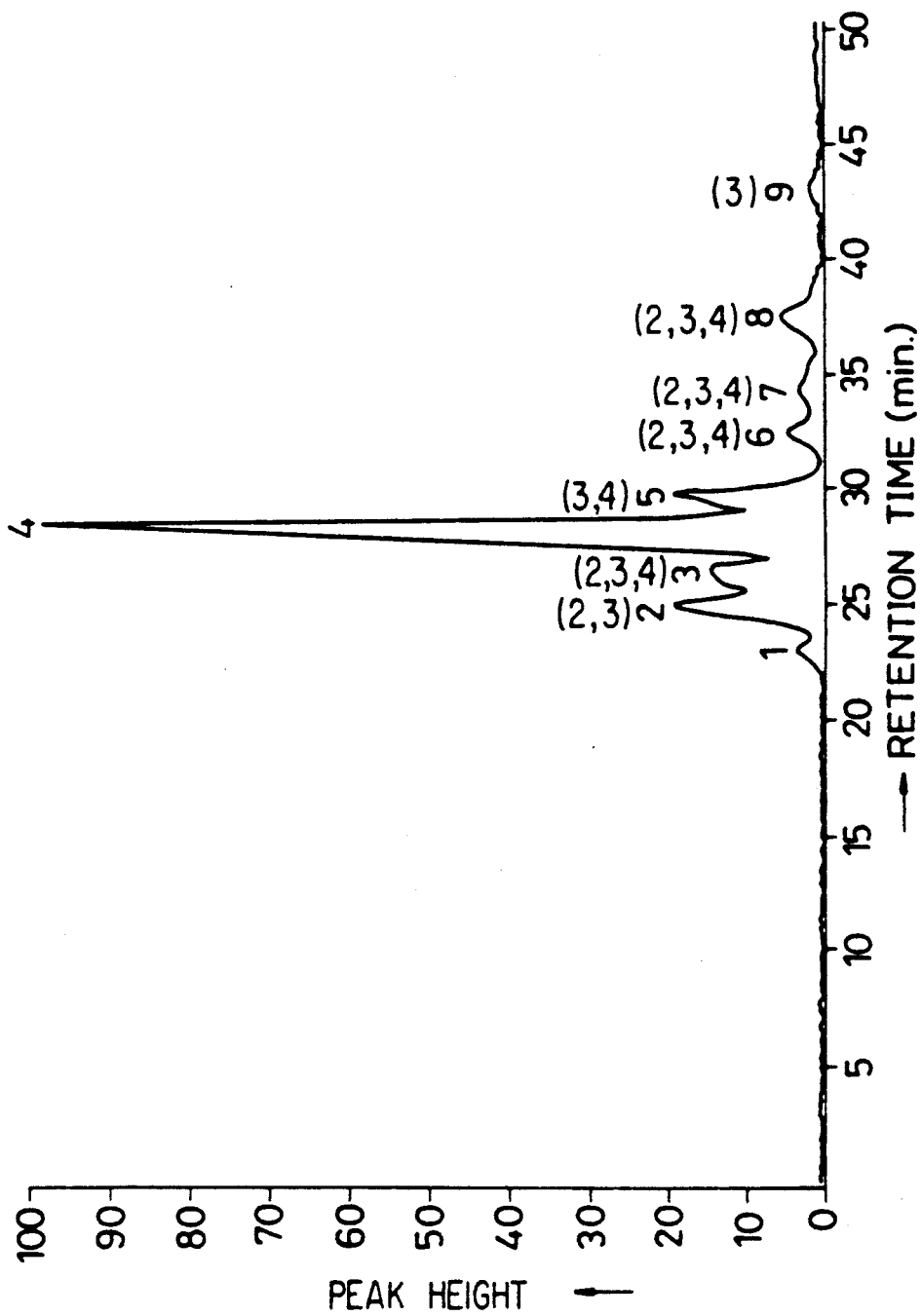

The mixture had a maximum absorption wavelength (λmax) of 715 nm. According to elementary analysis, the average bromination rate is 3.9 Br/molecule. FIG. 2 illustrates the chart of liquid chromatography and mass spectrometry. In FIG. 2, the number(s) in parentheses mean the content of bromine atom per molecule, for example, "(2,3)" above the peak 2 means that is composed of the mixture of double brominated molecule and triple brominated molecule.

EXAMPLE 14

Figure 3:
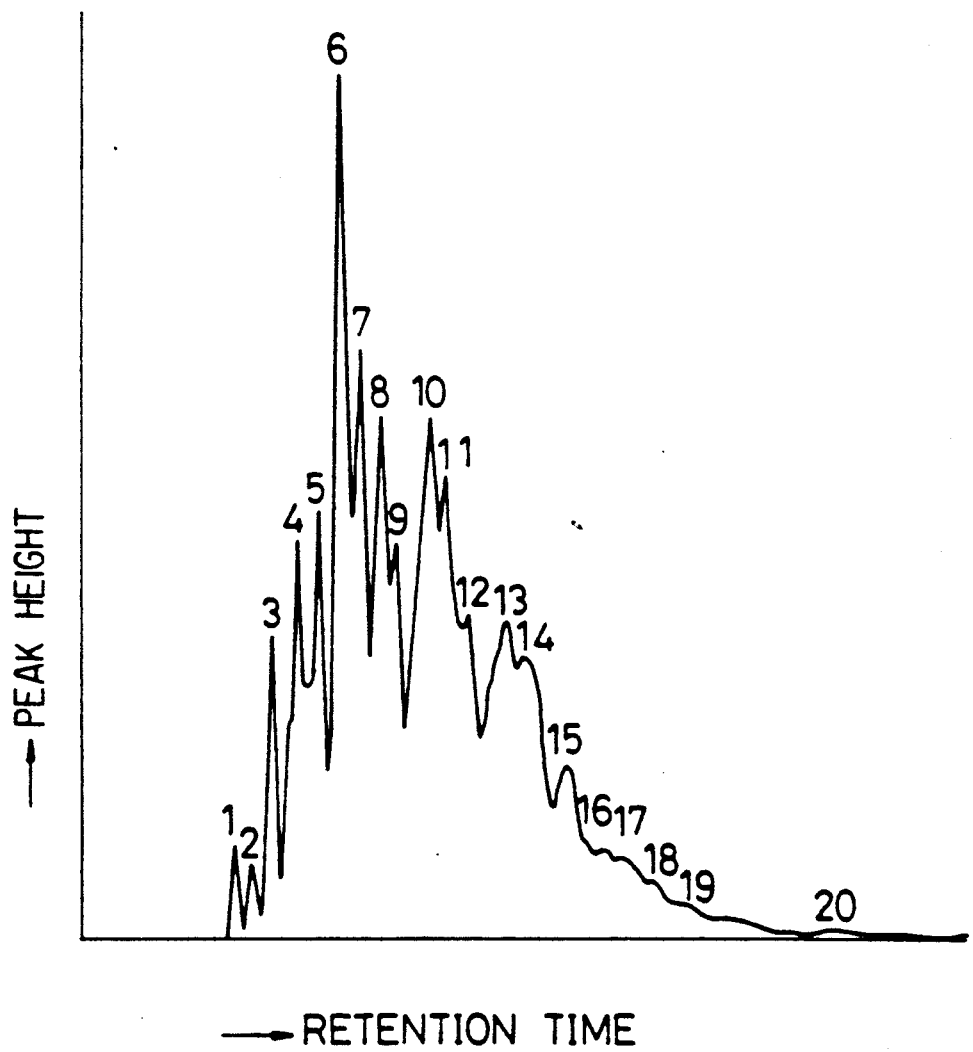

Ten parts of a mixture composed of the compounds having the below described formulas (27), (28), (29) and (30) in a (27)/(28)/(29)/(30) ratio of 20/40/30/10 were dissolved in 200 parts of carbon tetrachloride. A solution containing 6.3 parts of bromine in 200 parts of acetic acid was added at 50° C. to the solution of the above mixture and reacted at 55° C. for 4 hours. Thereafter 200 parts of a 10% aqueous sodium hydrogen sulfite solution were added to carry out bromine-removing treatment. Thereafter the carbon tetrachloride layer was washed with water and dried over anhydrous sodium sulfate. The carbon tetrachloride solution thus obtained was poured into methanol Precipitated crystals were filtered and A mixture of the compounds having the formulas (31), (32), (33) and (34) was obtained. Melting point of the mixture was 150° to 184° C. FIG. 3 shows the chart of liquid chromatography and Table 2 shows the concentration ratio of each peak in FIG. 3.

TABLE 2

| PKNO | RETENTION TIME | CONC. RATIO |
|------|----------------|-------------|
| 1    | 15.075         | 0.6327      |
| 2    | 16.145         | 0.7175      |
| 3    | 17.58          | 2.821       |
| 4    | 19.243         | 6.1435      |
| 5    | 20.652         | 5.2198      |
| 6    | 22.04          | 12.8936     |
| 7    | 23.403         | 6.8576      |
| 8    | 24.69          | 7.6944      |
| 9    | 25.717         | 4.3091      |
| 10   | 28.083         | 12.7387     |
| 11   | 29.045         | 7.6674      |
| 12   | 30.418         | 4.623       |
| 13   | 32.865         | 9.2166      |
| 14   | 34.158         | 7.3566      |
| 15   | 36.825         | 4.9525      |
| 16   | 39.292         | 1.5274      |
| 17   | 40.55          | 2.9945      |
| 18   | 44.47          | 1.0211      |
| 19   | 47.823         | 0.4812      |
| 20   | 54.423         | 0.1321      |
|      | TOTAL          | 100         |

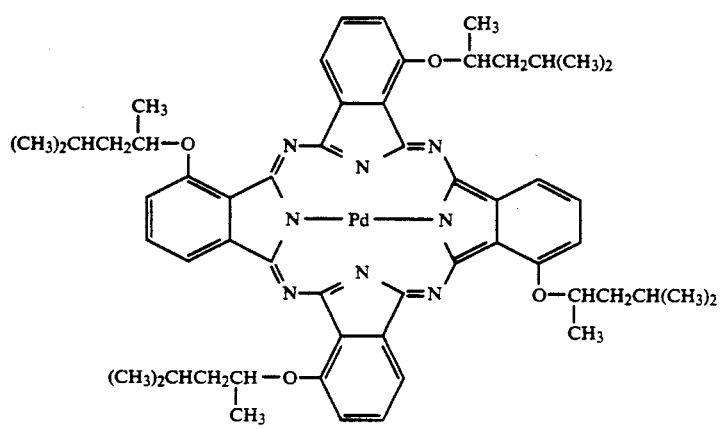
(27)
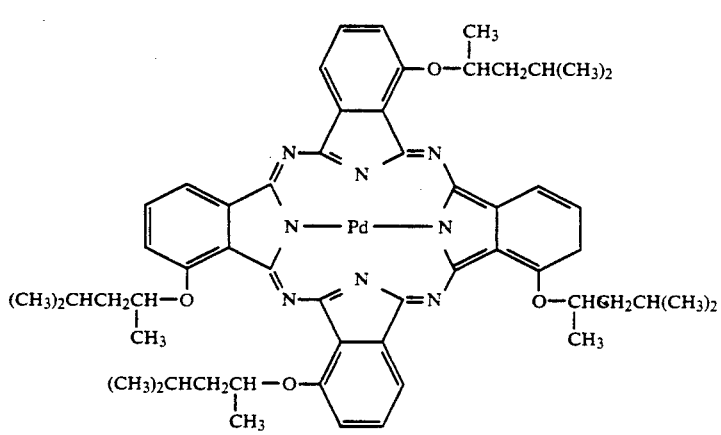
(28)
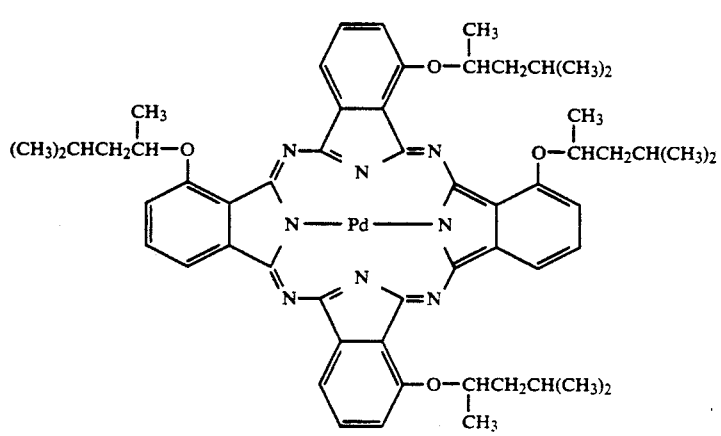
(29)

-continued
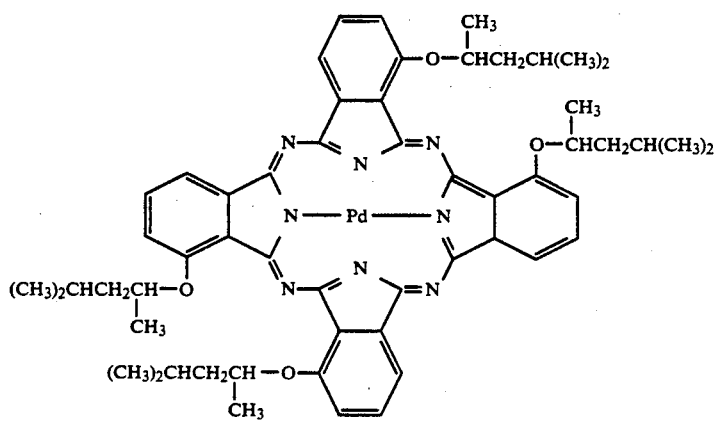
(30)
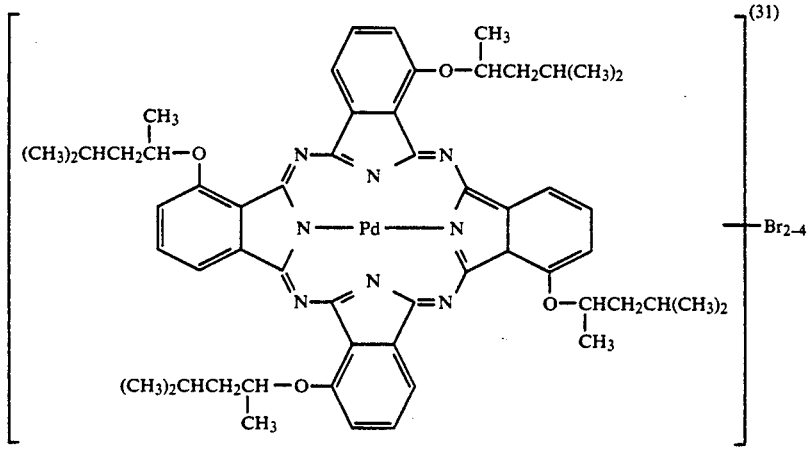
(31)
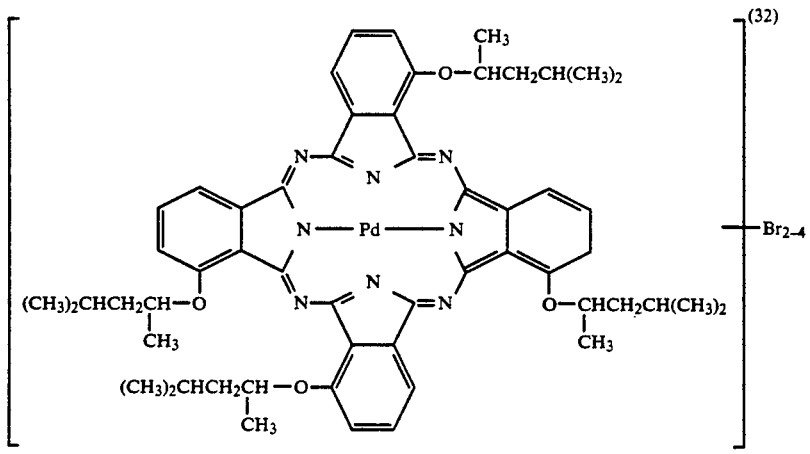
(32)

-continued

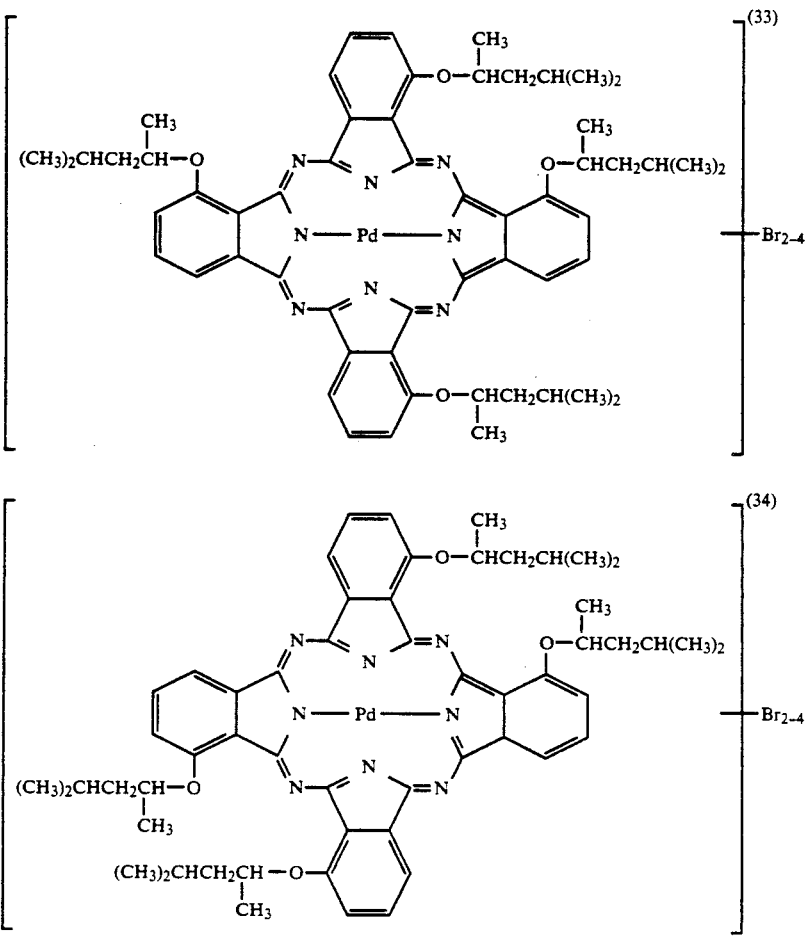

EXAMPLE 15

Ten grams of a mixture composed of the compounds having the below described formulas (35), (36) and (37) in a (35)/(36)/(37) ratio of 20/10/70 are dissolved in 400 g of carbon tetrachloride. To the solution, 25 g of bromine was added dropwise at 40° C. and reacted for one hour at 50° C. The reaction mixture was poured into 4 l of methanol. Eight grams of precipitated green crystals were filtered and recrystallized from dichloromethane/methanol.

The crystals thus purified had a maximum absorption wavelength ($\lambda$max) of 705 nm and a melting point of 201°–228° C. The mixture was composed of the compounds having the below described formulas (38), (39), (40), (41), (42), (43), (44), (45) and (46).

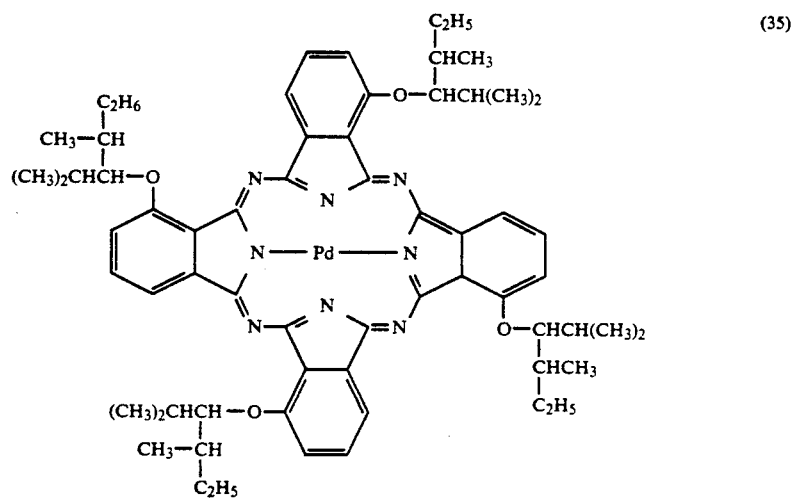

-continued
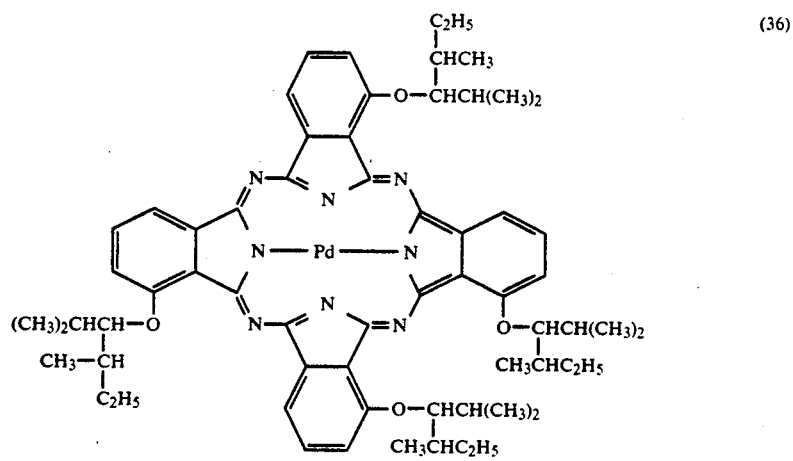
(36)
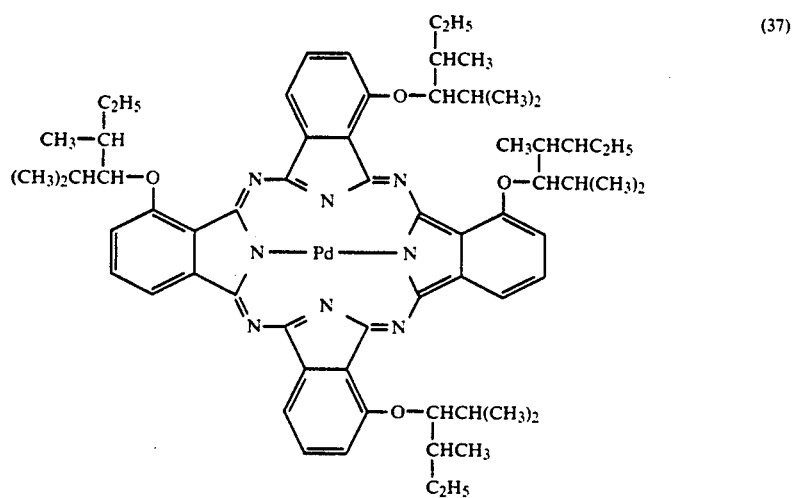
(37)
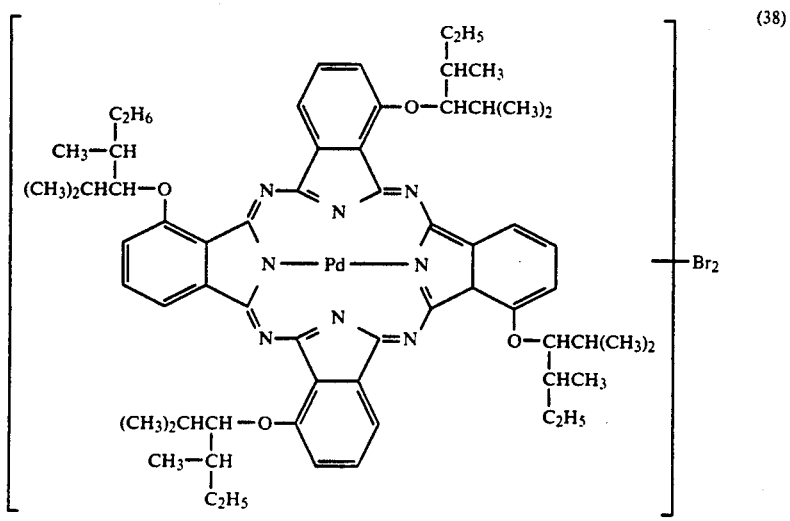
(38)

-continued
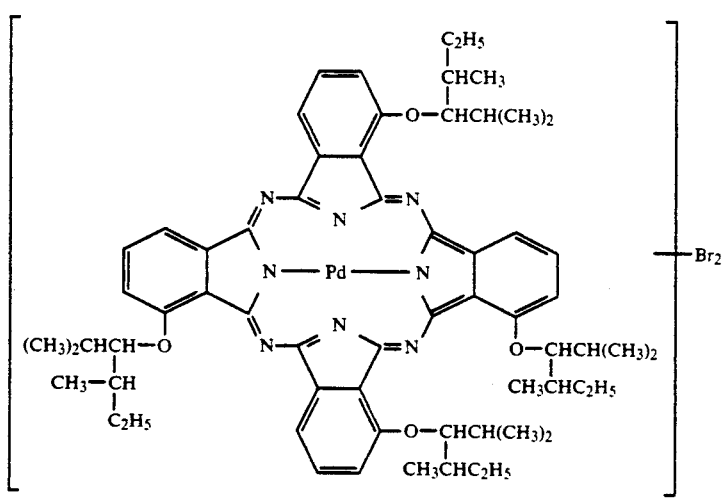
(39)
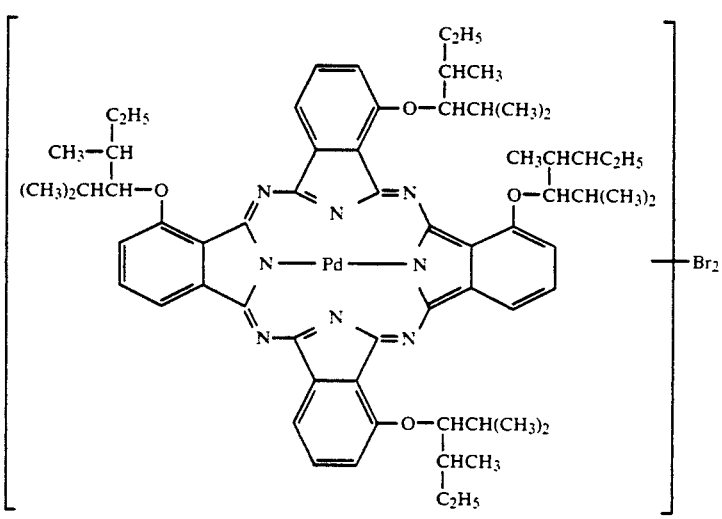
(40)
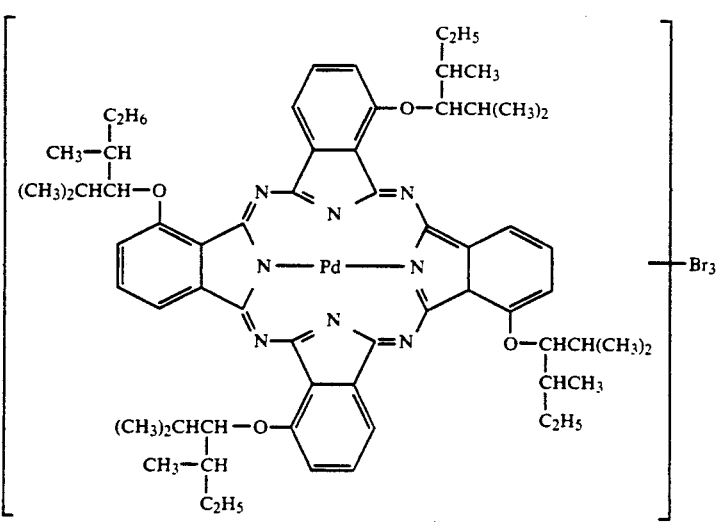
(41)

-continued
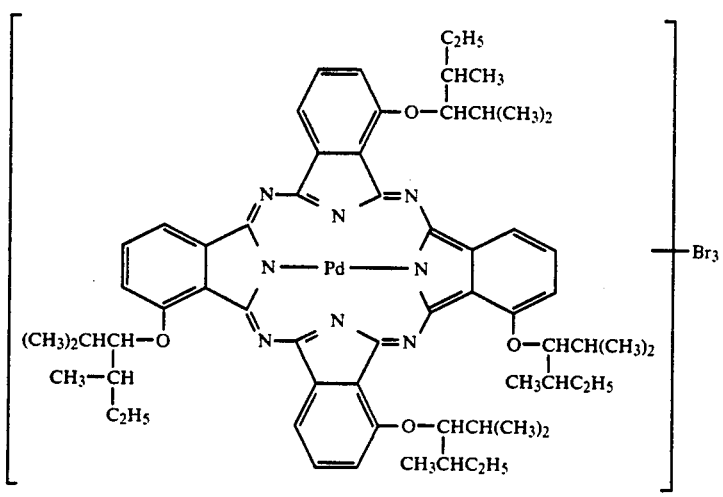
(42)
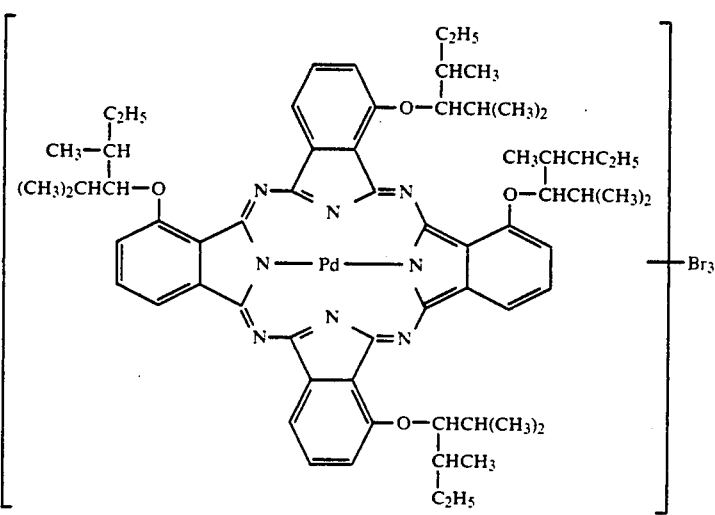
(43)
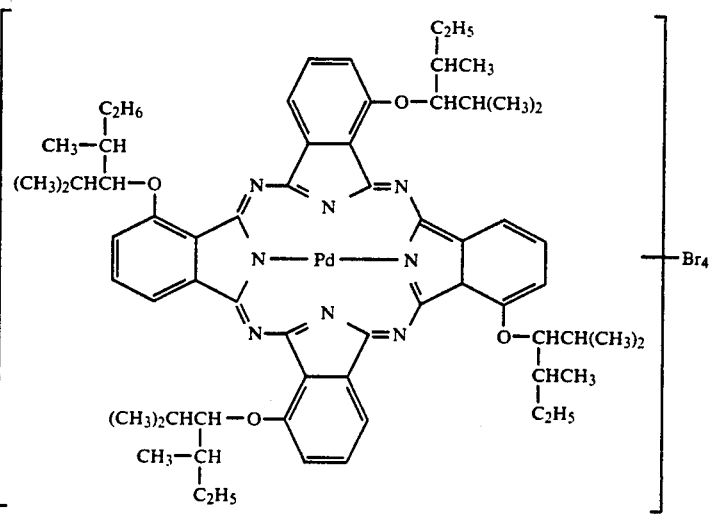
(44)

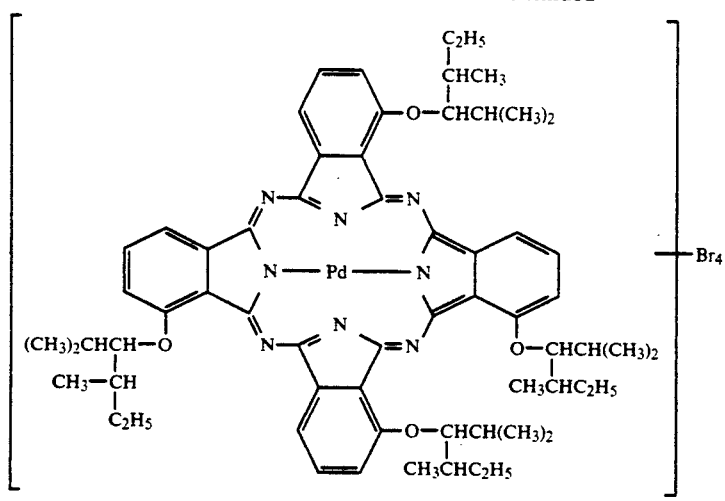

(45)

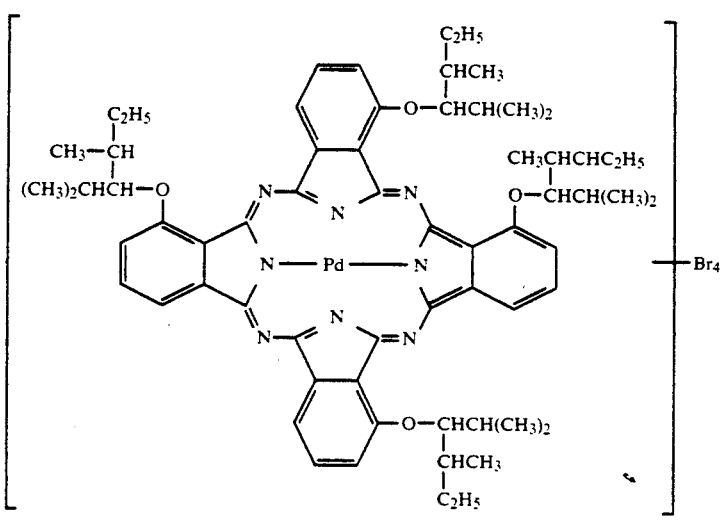

(46)

EXAMPLE 16

Ten grams of a mixture composed of the compounds having the below described formulas (47), (48) and (49) in a (47)/(48)/(49) ratio of 30/10/60 was dissolved in 200 g of chloroform. To the solution, 25 g of bromine was added dropwise at 40° C. and reacted at 50° C. for an hour. To the reaction mixture, 100 g of a 10% aqueous sodium hydrogen sulfite solution was added and stirred. After separating the chloroform layer from the water layer, the chloroform layer was poured into 4 l of methanol and a precipitated green solid was filtered. The solid has a maximum absorption wave length (λmax) of 707.5 nm and a melting point of 262°-286° C.

The solid was a mixture composed of the compounds having the below described formulas (50), (51), (52), (53), (54), (55), (56), (57) and (58).

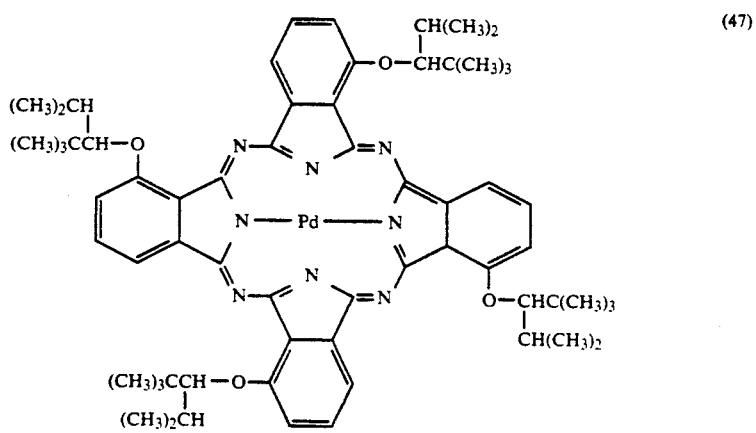

(47)

-continued
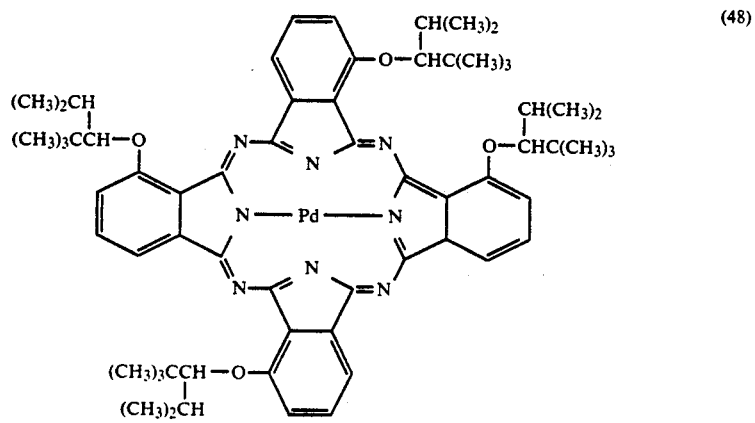 (48)
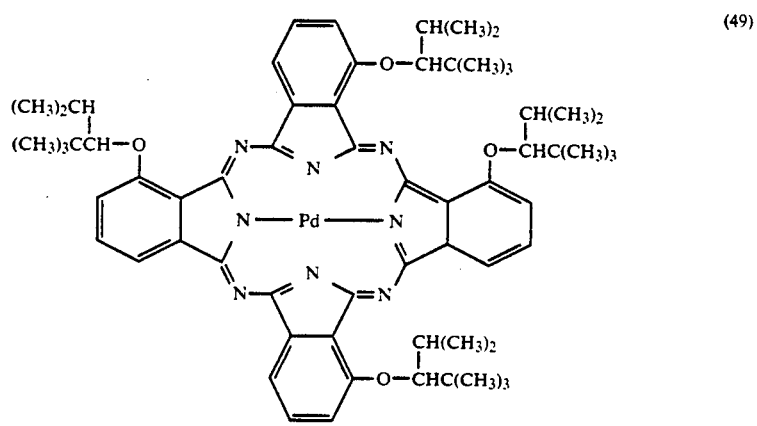 (49)
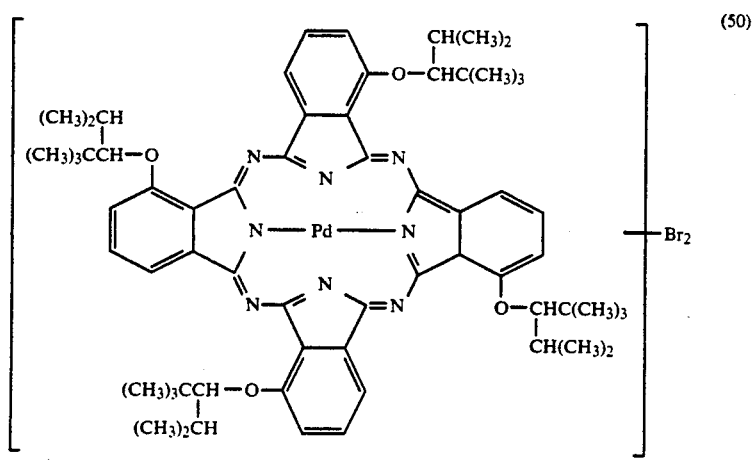 (50)

-continued
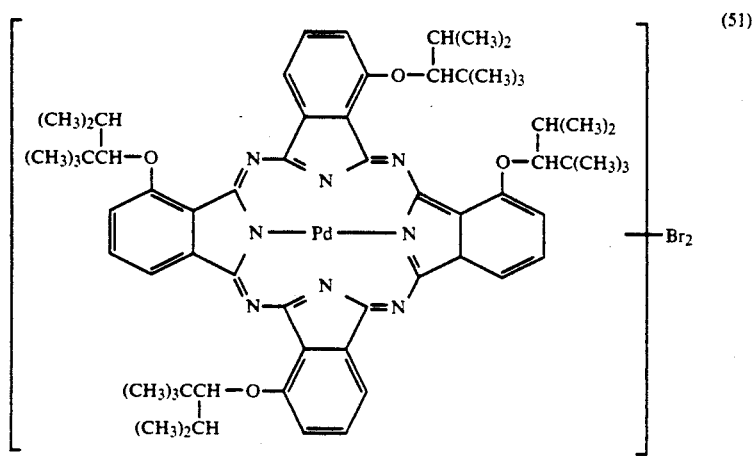
(51)
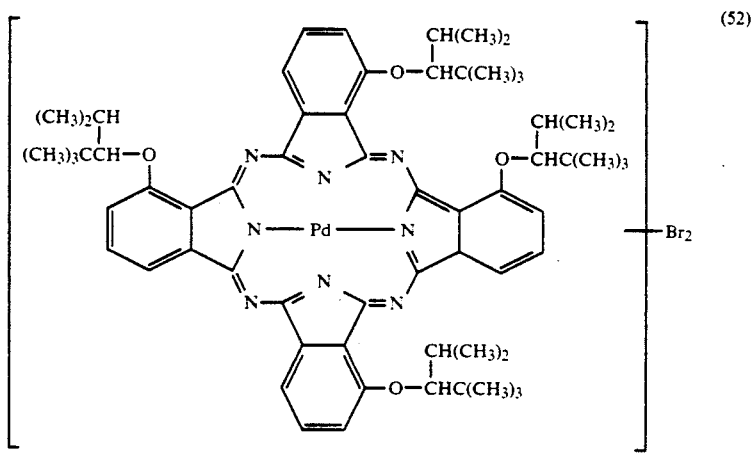
(52)
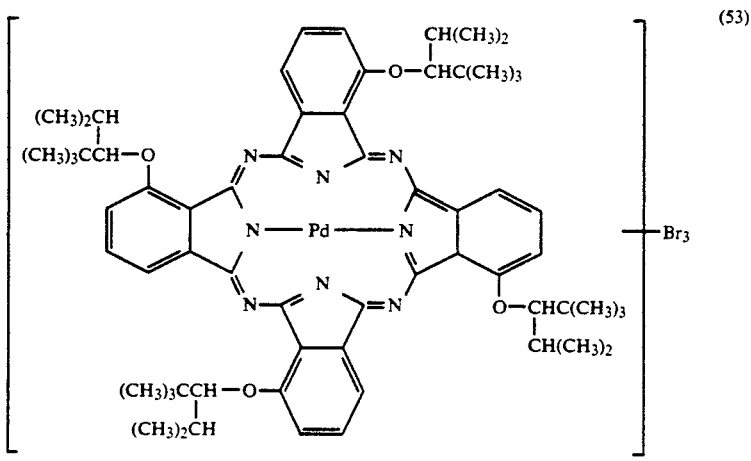
(53)

-continued
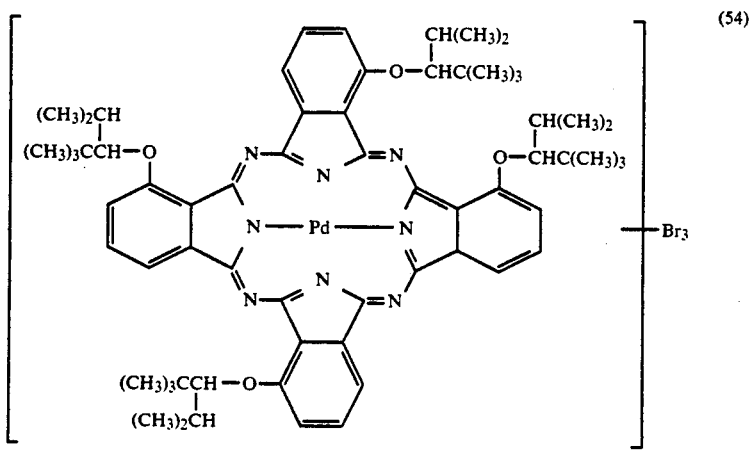
(54)
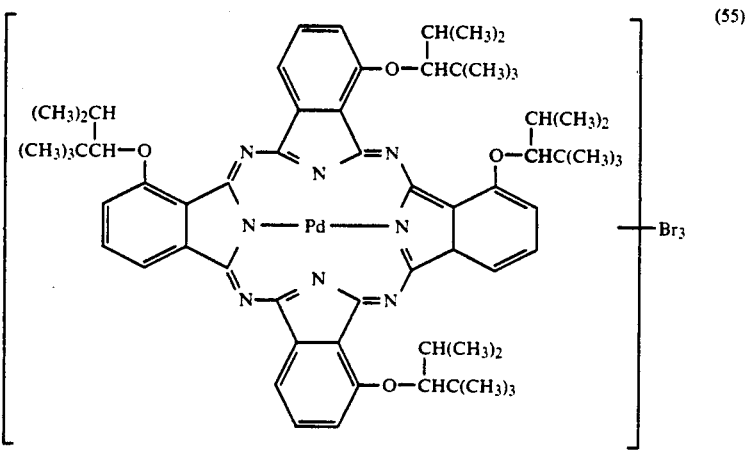
(55)
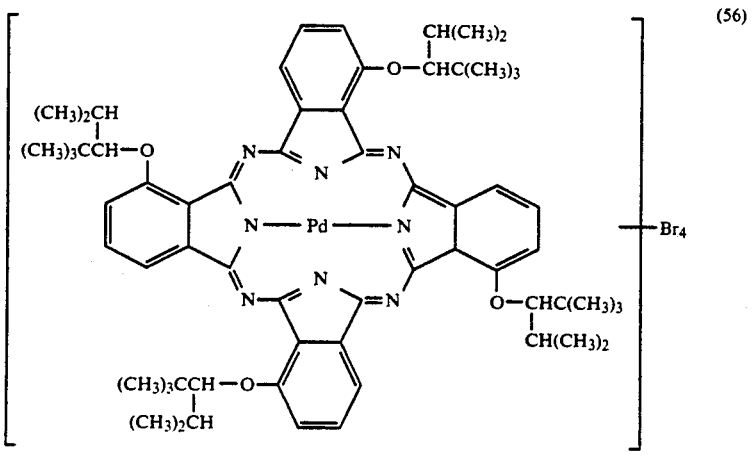
(56)

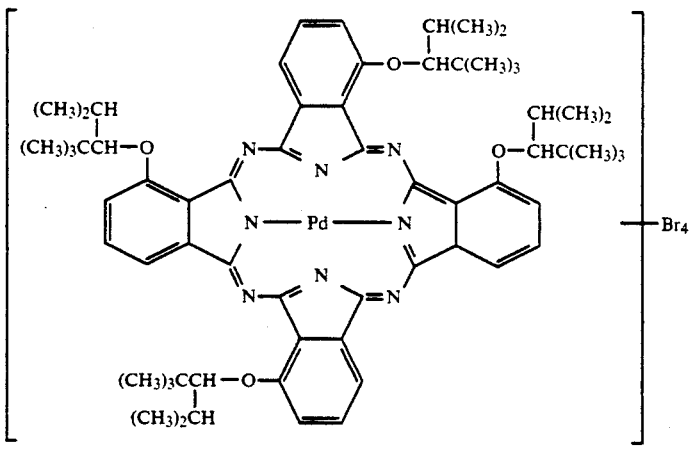

(57)

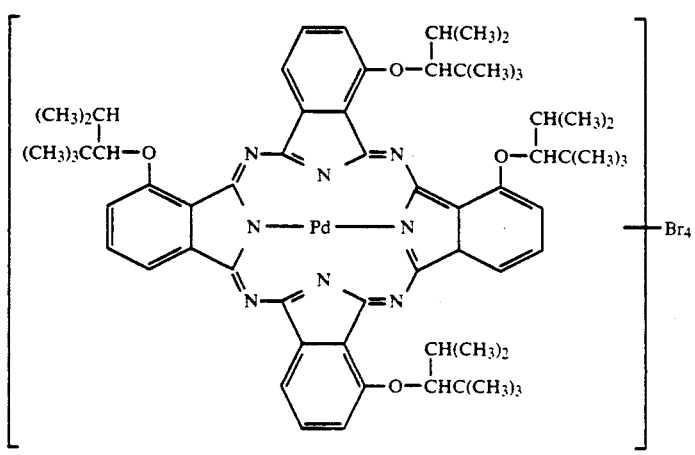

(58)

EXAMPLE 17

Two grams of palladium tetra-α-(2-ethylhexyloxy)-phthalocyanine were added to 400 ml of acetic acid and dissolved by warming to 40° C. Thereafter 5 g of bromine was added dropwise to the solution and stirred at 50° C. for an hour. The reaction mixture was cooled to 40° C. Precipitated crystals were filtered and sludged three times with 30 ml of methanol. The crystals thus obtained were dried under reduced pressure. The yield was 2.2 g. According to elementary analysis, the number of bromine substitution was between 2 and 3, and proved of a mixture consisting of 2 and 3 bromine-substituted phthalocyanine.

| | Elementary analysis: | | | |
|---|---|---|---|---|
| | C | H | N | Br |
| Calculated (%) | | | | |
| 2-substitution | 59.60 | 6.10 | 8.69 | 12.39 |
| 3-substitution | 56.17 | 5.67 | 8.19 | 17.52 |
| Found (%) | 57.89 | 5.90 | 8.44 | 14.96 |

EXAMPLE 18

Five grams of dichlorosilicone tetra-α-(2-ethylhexyloxy)phthalocyanine were added to 100 ml of acetic acid and dissolved by warming to 40° C. Thereafter 5 g of bromine was added dropwise to the solution and stirred at 50° C. for an hour. The reaction mixture was cooled to 40° C. Precipitated crystals were filtered and sludged three times with 100 ml of methanol. The crystals thus obtained were dried under reduced pressure. The yield was 5.2 g. According to elementary analysis, the number of bromine substitution was 3.

| Elementary analysis: $C_{64}H_{77}N_8O_4Br_3Cl_2Si$ | | | | |
|---|---|---|---|---|
| | C | H | N | Br | Cl |
| Calculated (%) | 56.48 | 5.70 | 8.23 | 17.61 | 5.21 |
| Found (%) | 57.03 | 5.81 | 8.35 | 17.00 | 5.40 |

EXAMPLE 19

Two grams of palladium tetra-α-(1,3-dimethylbutyloxy)phthalocyanine were added to 40 ml of acetic acid and dissolved by warming to 35° C. Then 2 g of sulfuryl chloride was added dropwise to the solution and stirred at 50° C. for 1.5 hours. The reaction mixture was cooled to 35° C. Precipitated crystals were filtered, washed twice with 50 ml of water, sludged three times with 50 ml of methanol, and dried under reduced pressure. The yield was 2.1 g. According to elementary analysis, the number of bromine substitution was 4.

| Elementary analysis: $C_{56}H_{60}N_8O_4Cl_4Pd$ | | | | |
|---|---|---|---|---|
| | C | H | N | Br |
| Calculated (%) | 58.11 | 5.23 | 9.68 | 12.25 |
| Found (%) | 57.78 | 5.03 | 9.61 | 12.63 |

What is claimed is:

1. A preparation process of a halogenated alkoxyphthalocyanine comprising reacting an alkoxyphthalocyanine represented by the formula (1):

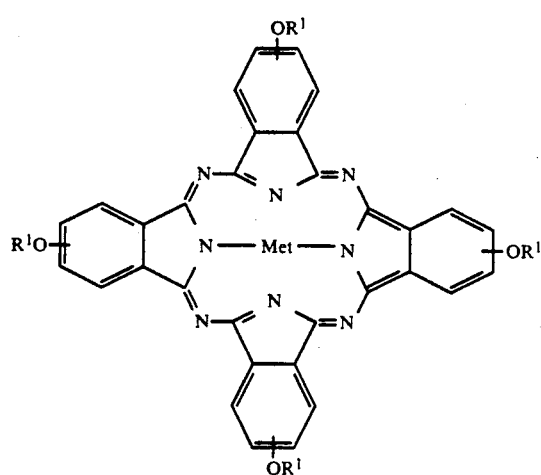

wherein $R^1$ is a substituted or unsubstituted alkyl group and may be the same or different, and Met is two hydrogen atoms, a divalent metal atom, or a trivalent or tetravalent metal derivative, with a halogenating agent represented by the formula (2):

$$X-Y \qquad (2)$$

wherein X is a halogen atom and Y is a residue of the halogenating agent selected from the group consisting of a halogen atom, $SO_2Cl$, $SOCl$, $FeCl_2$, $PCl_4$, $POCl_2$, CuBr and quaternary ammonium, to obtain the halogenated alkoxyphthalocyanine represented by the formula (3):

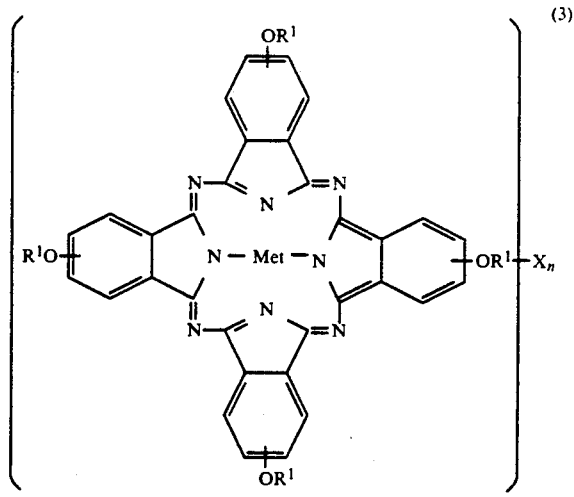

wherein $R^1$, Met and X are the same as $R^1$ and Met of formula (1) and X of formula (2), respectively, and n is the number of substitution of X and is an integer of from 1 to 4, said X's being attached to benzene rings attached to the phthalocyanine nucleus.

2. The preparation process of claim 1 wherein the alkoxyphthalocyanine is a single compound or a mixture of two or more compounds selected from the phthalocyanines having the formula (4) to formula (7):

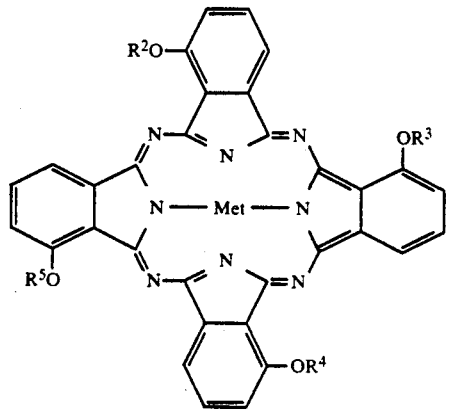

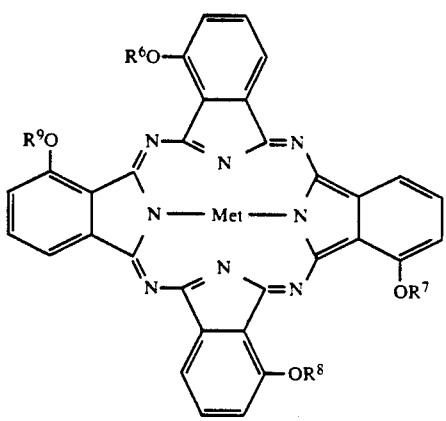

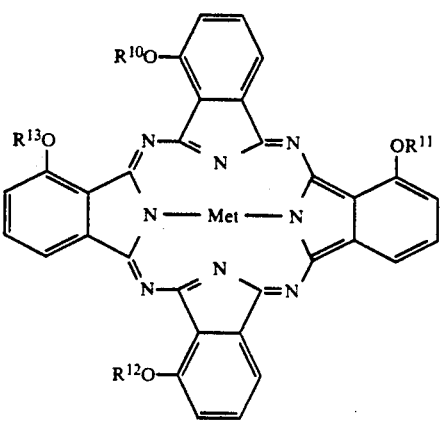

-continued (7)

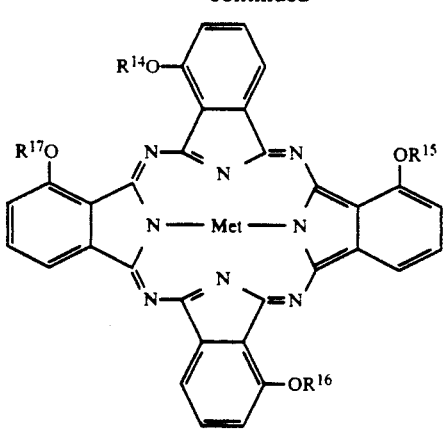

wherein each of R² to R¹⁷ is individually a substituted or unsubstituted alkyl group, and Met is two hydrogen atoms, a divalent metal atom, or a trivalent or tetravalent metal derivative.

3. The preparation process of claim 2 wherein R² to R¹⁷ in the formulas (4) to (7) are branched alkyl groups.

4. The preparation process of claim 3 wherein R² to R¹⁷ in formulas (4) to (7) are branched alkyl groups having the sum of 2 to 4 of secondary, tertiary and quaternary carbon atoms.

5. The preparation process of claim 1 wherein the halogenating agent has the formula (8):

$$Br-Y \qquad (8)$$

wherein Y is a residue of a brominating agent selected from the group consisting of a halogen atom, $SO_2Cl$, $SOCl$, $FeCl_2$, $PCl_4$, $POCl_2$, $CuBr$ and quaternary ammonium.

6. The preparation process of claim 5 wherein the halogenating agent is bromine.

7. The preparation process of claim 6 wherein the reaction is carried out in the presence of a halogenated hydrocarbon or acetic acid.

8. The preparation process of claim 7 wherein the reaction is carried out at a temperature from 0° to 250° C.

9. The preparation process of claim 8 wherein the reaction is carried out at a temperature from 20° to 120° C.

10. The preparation process of claim 7 wherein the amount of the solvent is from 1 to 1000 times by weight of the alkoxyphthalocyanine.

11. The preparation process of claim 10 wherein the amount of the solvent is from 5 to 100 times by weight of the alkoxyphthalocyanine.

12. The preparation process of claim 11 wherein the amount of the halogenating agent is from 1 to 6 mole ratio to the alkoxyphthalocyanine.

* * * * *